United States Patent
Plach et al.

[11] Patent Number: 5,718,840
[45] Date of Patent: Feb. 17, 1998

[54] BENZENE DERIVATIVES, AND LIQUID-CRYSTALLINE MEDIUM

[75] Inventors: Herbert Plach, Darmstadt; Detlef Pauluth, Ober-Ramstadt; Joachim Krause, Dieburg; Georg Weber, Erzhausen; Volker Reiffenrath, Rossdorf; Eike Poetsch, Mühltal, all of Germany

[73] Assignee: Merck Patent Gesellschaft Mit Beschrankter Haftung, Darmstadt, Germany

[21] Appl. No.: 691,413

[22] Filed: Aug. 2, 1996

Related U.S. Application Data

[63] Continuation of Ser. No. 362,574, filed as PCT/EP94/01364, Apr. 29, 1994, abandoned.

[30] Foreign Application Priority Data

May 10, 1993 [DE] Germany .................. 43 15 410.7
May 10, 1993 [DE] Germany .................. 43 15 553.7
May 10, 1993 [DE] Germany .................. 43 15 555.3

[51] Int. Cl.[6] ................ C09K 19/12; C09K 19/30; C09K 19/54
[52] U.S. Cl. ............... 252/299.66; 252/299.63; 252/299.01; 252/299.61; 252/299.62
[58] Field of Search ........... 252/299.66, 299.63, 252/299.01, 299.61, 299.62

[56] References Cited

U.S. PATENT DOCUMENTS 4,877,548 10/1989 Kitano et al. ............... 252/299.63
5,230,829 7/1993 Bartmann et al. ............ 252/299.63
5,308,542 5/1994 Poetsch et al. .............. 252/299.63
5,389,289 2/1995 Rieger et al. ............... 252/299.01
5,389,295 2/1995 Wachtler et al. ............ 252/299.63
5,397,505 3/1995 Rieger et al. ............... 252/299.67

FOREIGN PATENT DOCUMENTS 9117135 11/1991 European Pat. Off. .
507094 10/1992 European Pat. Off. .

*Primary Examiner*—C. H. Kelly
*Attorney, Agent, or Firm*—Millen, White, Zelano & Branigan, P.C.

[57] ABSTRACT

The invention relates to a liquid-crystalline medium based on a mixture of polar compounds of positive dielectric anisotropy, characterized in that it contains one or more compounds of the general formula I

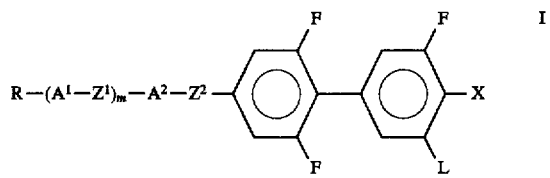

in which R, $A^1$, $A^2$, $Z^1$, $Z^2$, X, L and m are as defined in claim 1.

16 Claims, No Drawings

BENZENE DERIVATIVES, AND LIQUID-CRYSTALLINE MEDIUM

This application is a continuation of application Ser. No. 08/362,574, filed Jan. 9, 1995 now abandoned, which is a 371 of PCT/EP94/01364, filed Apr. 29, 1994, abandoned.

The present invention relates to benzene derivatives and to a liquid-crystalline medium, to the use of the latter for electrooptical purposes, and to displays containing this medium.

BACKGROUND OF INVENTION

Liquid crystals are used, in particular, as dielectrics in display devices since the optical properties of such substances can be effected by an applied voltage. Electrooptical devices based on liquid crystals are extremely well known to those skilled in the art and may be based on various effects. Devices of this type are, for example, cells having dynamic scattering, DAP (deformation of aligned phases) cells, guest/host cells, TN cells having a twisted nematic structure, STN (super-twisted nematic) cells, SBE (super-birefringence effect) cells and OMI (optical mode interference) cells. The most common display devices are based on the Schadt-Helfrich effect and have a twisted nematic structure.

The liquid-crystal materials must have good chemical and thermal stability and good stability toward electrical fields and electromagnetic radiation. Furthermore, the liquid-crystal materials should have low viscosity and give short addressing times, low threshold voltages and high contrast in the cells. Furthermore, they should have a suitable mesophase, for example, for the abovementioned cells, a nematic or cholesteric mesophase, at customary operating temperatures, i.e. in the broadest possible range above and below room temperature. Since liquid crystals are generally used as mixtures of a plurality of components, it is important that the components are readily miscible with one another. Further properties, such as electrical conductivity, dielectric anisotropy and optical anisotropy, must meet various requirements depending on the cell type and the area of application. For example, materials for cells having a twisted nematic structure should have positive dielectric anisotropy and low electrical conductivity.

For example, the media desired for matrix liquid-crystal displays containing integrated nonlinear elements for switching individual image points (MLC displays) are those having high positive dielectric anisotropy, broad nematic phases, relatively low birefringence, very high specific resistance good UV and temperature stability of the resistance and a low vapor pressure.

Matrix liquid-crystal displays of this type are known. Examples of nonlinear elements which can be used to individually switch the individual image points are active elements (i.e. transistors). This is then referred to as an "active matrix", and a differentiation can be made between two types:

1. MOS (Metal Oxide Semiconductor) or other diodes on a silicon wafer as substrate.
2. Thin-film transistors (TFTs) on a glass plate as substrate.

The use of monocrystalline silicon as the substrate material limits the display size since even the modular assembly of the various part displays results in problems at the joints.

In the case of the more promising type 2, which is preferred, the electrooptical effect used is usually the TN effect. A differentiation is made between two technologies: TFTs comprising compound semiconductors, such as, for example, CdSe, or TFTs based on polycrystalline or amorphous silicon. Intensive research efforts are being made worldwide in the latter technology.

The TFT matrix is applied to the inside of one glass plate of the display, while the inside of the other glass plate carries the transparent counterelectrode. Compared with the size of the image point electrode, the TFT is very small and hardly affects the image at all. This technology can also be extended to fully color-compatible image displays, where a mosaic of red, green and blue filters is arranged in such a manner that each filter element is located opposite a switchable image element.

The TFT displays usually operate as TN cells with crossed polarizers in transmission and are illuminated from the back.

The term MLC display here covers any matrix display containing integrated nonlinear elements, i.e. in addition to the active matrix, also displays containing passive elements such as varistors or diodes (MIM=metal-insulator-metal).

MLC displays of this type are particularly suitable for TV applications (for example pocket TV sets) or for high-information displays for computer applications (laptops) and in automobile or aircraft construction. In addition to problems with respect to the angle dependency of the contrast and the switching times, problems result in MLC displays due to inadequate specific resistance of the liquid-crystal mixtures TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288, Matrix LCD Controlled by Double Stage Diode Rings, p. 141 ff., Paris; STROMER, M., Proc. Eurodisplay 84, September 1984: Design of Thin Film Transistors for Matrix Adressing of Television Liquid Crystal Displays, p. 145 ff., Paris. As the resistance decreases, the contrast of an MLC display worsens and the problem of "afterimage elimination" may occur. Since the specific resistance of the liquid-crystal mixture generally decreases over the life of an MLC display due to interactions with the internal surfaces of the display, a high (initial) resistance is very important to give acceptable service lives. In particular in the case of low-voltage mixtures, it was hitherto not possible to achieve very high specific resistances. It is furthermore important that the specific resistance increases as little as possible with increasing temperature and after heating and/or exposure to UV radiation. The low-temperature properties of the mixtures from the prior art are also particularly disadvantageous. It is required that crystallization and/or smectic phases do not occur, even at low temperatures, and that the temperature dependence of the viscosity is as low as possible. The MLC displays of the prior art thus do not satisfy current demands.

Thus, there continues to be a great demand for MLC displays of very high specific resistance and at the same time a broad operating temperature range, short switching times, even at low temperatures and low threshold voltage which do not have these disadvantages or only do so to a lesser extent.

For TN (Schadt-Helfrich) cells, media are desired which facilitate the following advantages in the cells:

broadened nematic phase range (in particular down to low temperatures), switchability at extremely low temperatures (outdoor use, automobiles, avionics), increased stability to UV radiation (longer life).

The media available from the prior art do not make it possible to achieve these advantages whilst simultaneously retaining the other parameters.

For supertwisted (STN) cells, media are desired which have a greater multiplexing ability and/or lower threshold voltages and/or broader nematic phase ranges (in particular at low temperatures). To this end, a further extension of the parameter latitude available (clearing point, smectic-nematic transition or melting point, viscosity, dielectric values, elastic values) is urgently desired.

SUMMARY OF THE INVENTION

The invention has the object of providing media, in particular for MLC, TN or STN displays of this type, which do not have the abovementioned disadvantages or only do so to a lesser extent, and preferably at the same time have very high specific resistances and low threshold voltages.

It has now been found that this object can be achieved if media according to the invention are used in displays.

The invention thus relates to a liquid-crystalline medium based on a mixture of polar compounds having positive dielectric anisotropy, characterized in that it contains one or more compounds of the general formula I

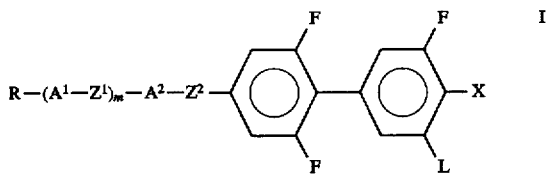

in which

R is H, an alkyl or alkenyl radical having 1 to 15 carbon atoms which is unsubstituted, monosubstituted by CN or $CF_3$ or at least monosubstituted by halogen, it also being possible for one or more $CH_2$ groups in these radicals to be replaced, in each case independently of one another, by —O—, —S—, —◊—, —CO—, —CO—O—, —O—CO— or —O—CO—O—, in such a way that O atoms are not linked directly to one another $A^1$ and $A^2$ are each, independently of one another, a
(a) trans-1,4-cyclohexylene radical in which, in addition, one or more non-adjacent $CH_2$ groups may be replaced by —O— and/or —S—,
(b) 1,4-phenylene radical in which, in addition, one or two CH groups may be replaced by N, or
(c) radical from the group consisting of 1,4-cyclohexenylene, 1,4-bicyclo(2,2,2)-octylene, piperidine-1,4-diyl, naphthalene-2,6-diyl, decahydronaphthalene-2,6-diyl and 1,2,3,4-tetrahydronaphthalene-2,6-diyl, it being possible for the radicals (a) and (b) to be substituted by one or two fluorine atoms, $Z^1$ and $Z^2$ are each, independently of one another, —CO—O—, —O—CO—, —CH$_2$O—, —OCH$_2$—, —CH$_2$CH$_2$—, —CH=CH—, —C≡C— or a single bond, and one of the radicals $Z^1$ and $Z^2$ is alternatively —(CH$_2$)$_4$— or —CH=CH—CH$_2$CH$_2$—, X is halogenated alkyl, alkoxy, alkenyl or alkenyloxy, in each case having 1 to 6 carbon atoms, L is F and also H when X is $OCF_3$, $OCF_2H$ or $OC_2F_5$, and m is 0, 1 or 2.

Particular preference is given to mixtures containing compounds of the formula I and all sub-formulae in which $A^1$ is 1,4-phenylene which is mono-substituted or disubstituted by F or monosubstituted by CN. These are in particular 2-fluoro-1,4-phenylene, 3-fluoro-1,4-phenylene, 3,5-difluoro-1,4-phenylene, 2-cyano-1,4-phenylene and 3-cyano-1,4-phenylene.

In the formula I, $Z^1$ and $Z^2$ are preferably a single bond and —CH$_2$CH$_2$—, secondarily preferably —CH$_2$O—, —OCH$_2$—, —O—CO— and —CO—O—. If one of the radicals $Z^1$ and $Z^2$ is —(CH$_2$)$_4$— or —CH=CH—CH$_2$CH$_2$—, the other radical $Z^1$ or $Z^2$ (if present) is preferably the single bond.

If R is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkyl radical in which one $CH_2$ group has been replaced by —CH=CH—, this may be straight-chain or branched. It is preferably straight-chain and has 2 to 10 carbon atoms. It is accordingly in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

They are accordingly in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkyl radical in which one $CH_2$ group has been replaced by unsubstituted or substituted-CH=CH— and an adjacent $CH_2$ group has been replaced by CO or CO—O or O—CO, this may be straight-chain or branched. It is preferably straight-chain and has 4 to 13 carbon atoms. It is accordingly in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or $CF_3$, this radical is preferably straight-chain. The substitution by CN or $CF_3$ is in any desired position.

If R is an alkyl or alkenyl radical which is at least monosubstituted by halogen, this radical is preferably straight-chain and halogen is preferably F or Cl. In the case of multiple substitution, halogen is preferably F. The resulting radicals also include perfluorinated radicals. In the case of monosubstitution, the fluorine or chlorine substituent may be in any desired position, but is preferably in the ω-position.

Compounds of the formula I which contain wing groups R which are suitable for polymerization reactions are suitable for the preparation of liquid-crystalline polymers.

Compounds of the formula I containing branched wing groups R may occasionally be of importance due to better solubility in the customary liquid-crystalline base materials, but in particular as chiral dopes if they are optically active. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R is an alkyl radical in which two or more $CH_2$ groups have been replaced by —O— and/or —CO—O—, this may be straight-chain or branched. It is preferably branched and has 3 to 12 carbon atoms. It is accordingly in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

The 1,4-cyclohexenylene group preferably has the following structures:

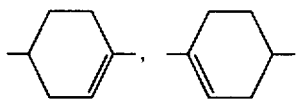

The invention also relates to novel compounds of the formulae I1 and I2:

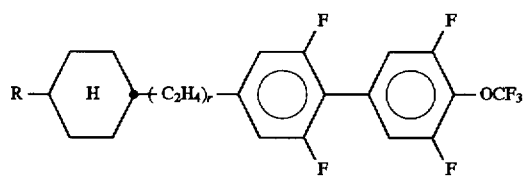

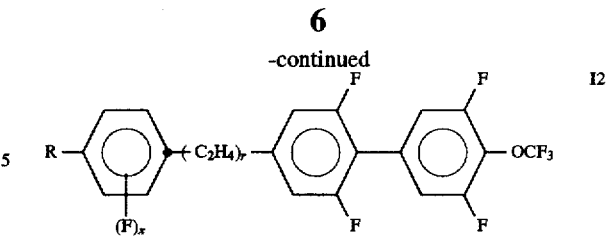

in which

R is as defined above, and r is 0 or 1, and x is 0, 1 or 2.

Some compounds of the formulae I1 and I2 are covered by the general formulae in WO 89/02884, WO 91/03450 and WO 91/08184. However, the advantageous effects of tetrafluorobiphenyls as components of liquid-crystalline media are not mentioned.

The compounds of the formulae I1 and I2 can, like similar compounds, for example known from WO 89/02884, be used as components of liquid-crystalline media, in particular for displays based on the principle of the twisted cell. They have a broad range of applications. Depending on the choice of substituents, these compounds can be used as base materials of which the liquid-crystalline media are predominantly composed; however, compounds of the formula I can also be added to liquid-crystalline base materials from other classes of compound in order, for example, to modify the dielectric and/or optical anisotropy of dielectrics of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The preferred radicals for compounds of the formula I also apply to the compounds I1 and I2.

The compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and suitable for said reactions.

Use may also be made here of variants which are known per se, but are not described here in greater detail.

The compounds according to the invention can be prepared, for example, by metallating a compound of formula II*

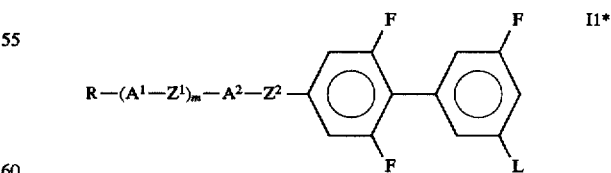

in which R, $A^1$, $A^2$, $Z^1$, $Z^2$, L and m are as defined above, in accordance with the reaction scheme below, and subsequently reacting the product with a suitable electrophile.

The compounds of the formulae I1 and I2 can be prepared as follows:

Scheme 1

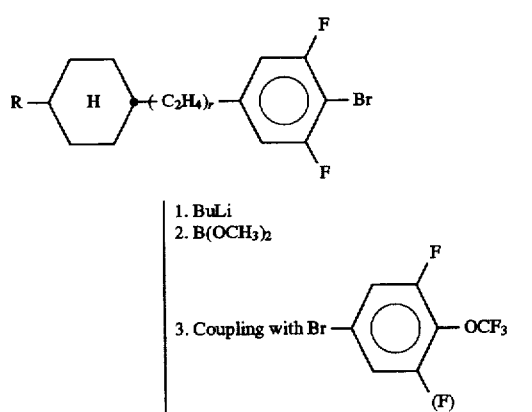

Scheme 2

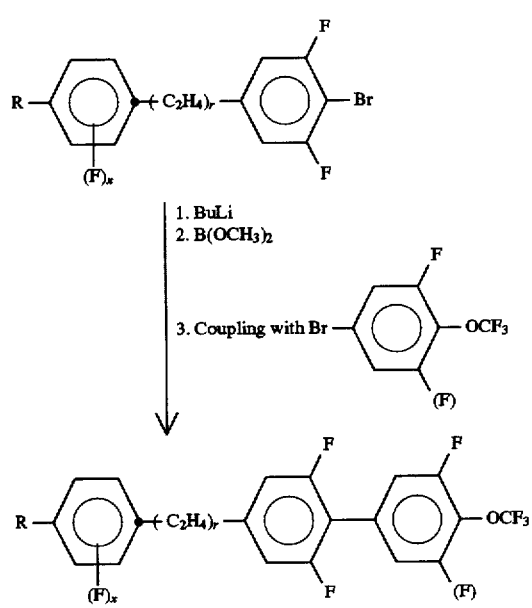

Compounds of the formula I in which R is $OC_2F_5$ can be prepared, for example, as follows:

Scheme 3

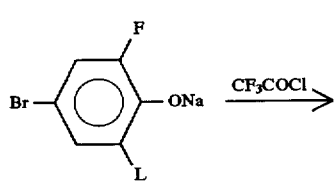

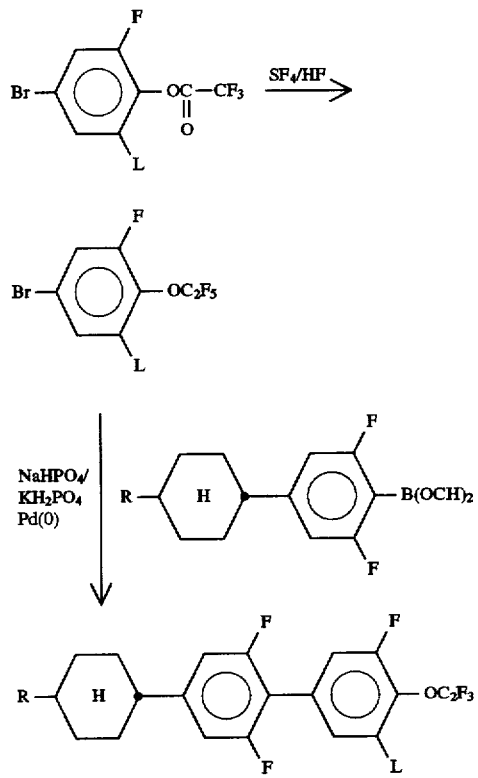

Further synthetic methods are evident to the person skilled in the art. For example, appropriately 5-substituted 1,3-difluorobenzene compounds or monofluorinated analogues (L=H) can be converted into the 1,3-difluoro compounds or monofluorinated analogues (L=H) in accordance with the above scheme, and the radical $R—(A^1—Z^1)_m$ can subsequently be introduced by reactions which are customary in liquid-crystal chemistry (for example esterification, etherification or coupling, for example as described in the article by E. Poetsch, Kontakte (Darmstadt), 1988 (2), p. 15).

The compounds of the formula II* can be prepared, for example, in accordance with the synthetic schemes below:

Scheme 4

$(A = +A^1—Z^1)_m—A^2, L = H$ or $F)$

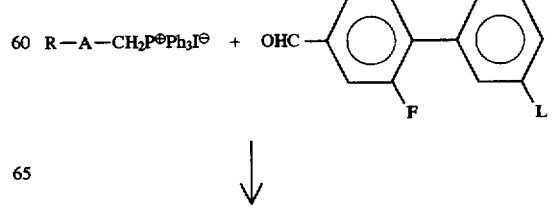

-continued
Scheme 4

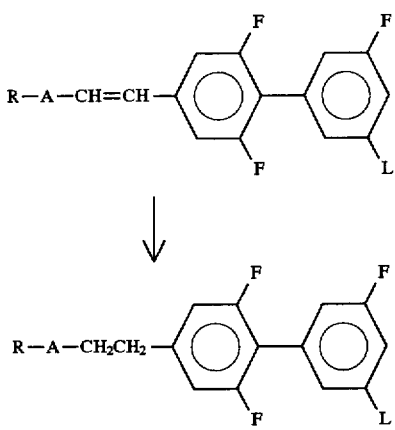

Scheme 5

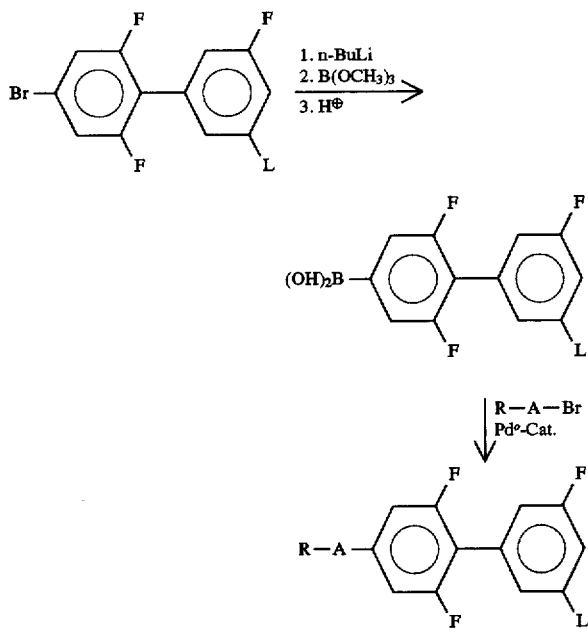

Starting materials are either known or can be prepared analogously to known compounds.

Esters of the formula I can also be obtained by esterifying corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known or can be prepared analogously to known processes.

In a further process for the preparation of the compounds of the formula I, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines necessary for the success of the coupling reaction, such as, for example, triethylamine, are also suit-able as solvent. Examples of suitable palladium catalysts are palladium salts, in particular Pd(II) acetate, with organophosphorus(III) compounds, such as, for example, triarylphosphines. The reaction can be carried out in the presence or absence of an inert solvent at temperatures between about 0° and 150°, preferably between 20° and 100°; examples of suitable solvents are nitriles, such as acetonitrile, or hydrocarbons, such as benzene or toluene. The aryl halides and olefins employed as starting materials are in many cases commercially available or can be prepared by processes known from the literature, for example by halogenation of corresponding parent compounds or by elimination reactions on corresponding alcohols or halides.

In this way, for example, stilbene derivatives can be prepared. The stilbenes can furthermore be prepared by reacting a 4-substituted benzaldehyde with a corresponding phosphorus ylide by the Wittig method. However, tolans of the formula I can also be prepared by employing monosubstituted acetylene instead of the olefin (Synthesis 627 (1980) or Tetrahedron Lett. 27, 1171 (1986)).

Aromatic compounds can furthermore be coupled by reacting aryl halides with aryltin compounds. These reactions are preferably carried out with addition of a catalyst, such as, for example, a palladium(O) complex, in inert solvents, such as hydrocarbons, at high temperatures, for example in boiling xylene, under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I can also be prepared by the Fritsch-Buttenberg-Wiechell rearrangement (Ann. 279, 319, 1984), in which the 1,1-diaryl-2-haloethylenes are rearranged to diarylacetylenes in the presence of strong bases.

Tolans of the formula I can also be prepared by brominating the corresponding stilbenes and then subjecting the products to dehydrohalogenation. Use may be made here of variants which are known per se, but are not described here in greater detail.

Ethers of the formula I are obtainable by etherifying the corresponding hydroxyl compounds, preferably corresponding phenols, the hydroxyl compound expediently first being converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This can then be reacted with the corresponding alkyl halide, alkyl sulphonate or dialkyl sulphate, expediently in an inert solvent, such as, for example, acetone, 1,2-dimethoxyethane, DMF or dimethyl sulphoxide, or alternatively with an excess of aqueous or aqueous-alcoholic NaOH or KOH, at temperatures between about 20° and 100° C.

The compounds of the formula I in which R=alkenyl can be obtained from the corresponding cyano compounds (R=CN), which are converted into the aldehydes (R=CHO) using diisobutylaluminum. For example, in successive steps, a methylene group can be introduced by a Wittig reaction of the aldehyde with methoxymethyl-triphenylphosphonium chloride, followed by hydrolysis of the resultant enol ether (for example using dilute hydrochloric acid).

The starting materials are either known or can be prepared analogously to known compounds.

The compounds having a —(CH$_2$)$_4$— bridge can be prepared in accordance with the following scheme:

Scheme 6

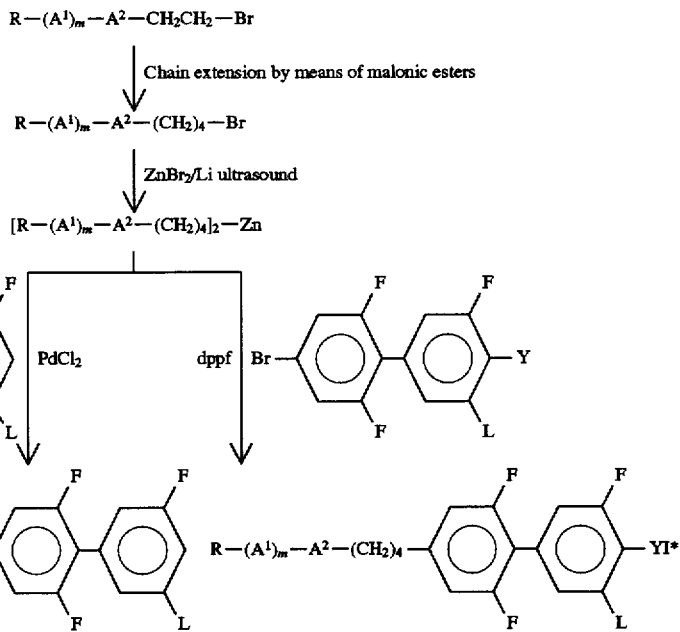

In the Pd(II)-catalyzed coupling reaction, either the target product I* is formed directly or a precursor is formed into which the radical —Y is introduced entirely analogously to the above methods for compounds of the formula I.

The compounds having a —CH=CH—CH$_2$CH$_2$— bridge can be prepared by the Wittig method in accordance with the following scheme:

Scheme 7

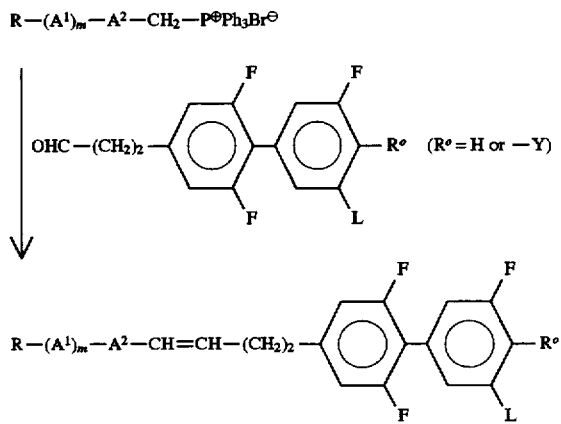

The invention also relates to electrooptical displays (in particular STN or MLC displays having two plane-parallel outer plates which, together with a frame, form a cell, integrated nonlinear elements for switching individual image points on the outer plates, and a nematic liquid-crystal mixture of positive dielectric anisotropy and high specific resistance located in the cell) which contain media of this type, and to the use of these media for electrooptical purposes.

The liquid-crystal mixtures according to the invention facilitate a significant broadening of the parameter latitude available.

The achievable combinations of clearing point, viscosity at low temperature, thermal and UV stability and dielectric anisotropy are far superior to the previous materials from the prior art.

The requirement for a high clearing point, a nematic phase at low temperature and a high Δε was previously only achievable to an unsatisfactory extent. Although systems such as, for example, ZLI-3119 have a comparable clearing point and comparatively favorable viscosities, they have, however, a Δε of only +3.

Other mixture systems have comparable viscosities and values of Δε, but only have clearing points in the region of 60° C.

The liquid-crystal mixtures according to the invention make it possible, while retaining the nematic phase at down to −20° C. and preferably down to −30° C., particularly preferably down to −40° C., to achieve clearing points above 80°, preferably above 90°, particularly preferably above 100° C., simultaneously dielectric anisotropy values Δε≧6, preferably ≧8, and a high value for the specific resistance, which means that excellent STN and MCL displays can be achieved. The mixtures are characterized in particular by low operating voltages. The TN thresholds (VIP) are below 2.0 V, preferably below 1.5 V, particularly preferably <1.3 V.

It goes without saying that a suitable choice of the components of the mixtures according to the invention also allows higher clearing points (for example above 110°) to be achieved at higher threshold voltages or lower clearing points to be achieved at lower threshold voltages while retaining the other advantageous properties. It is likewise possible to obtain mixtures of relatively high Δε and thus lower thresholds if the viscosities are increased by a correspondingly small amount. The MLC displays according to the invention preferably operate in the first transmission minimum of Gooch and Tarry [C. H. Gooch and H. A. Tarry, Electron. Lett. 10, 2–4, 1974; C. H. Gooch and H. A. Tarry, Appl. Phys., Vol. 8, 1575–1584, 1975]; in this case, a lower dielectric anisotropy in the second minimum is sufficient in addition to particularly favorable electrooptical properties.

such as, for example, high gradient of the characteristic line and low angle dependency of the contrast (German Patent 30 22 818) at the same threshold voltage as in an analogous display. This allows significantly higher specific resistances to be achieved in the first minimum using the mixtures according to the invention than using mixtures containing cyano compounds. A person skilled in the art can use simple routine methods to produce the birefringence necessary for a prespecified layer thickness of the MLC display by a suitable choice of the individual components and their proportions by weight.

The viscosity at 20° C. is preferably <60 mPa.s, particularly preferably <50 mPa.s. The nematic phase range is preferably at least 90°, in particular at least 100°. This range preferably extends at least from −20° to +80°.

Measurements of the "capacity holding ratio" (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention containing compounds of the formula I exhibit a considerably smaller decrease in the HR with increasing temperature than do analogous mixtures in which the compounds of the formula I are replaced by cyanophenylcyclohexanes of the formula

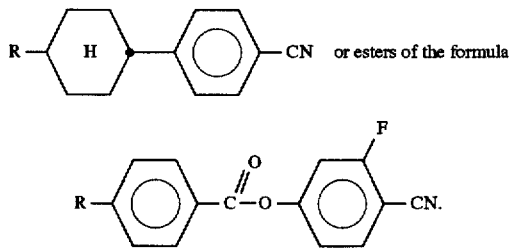

The UV stability of the mixtures according to the invention is also considerably better, i.e. they exhibit a significantly smaller decrease in the HR on exposure to UV radiation.

The media according to the invention are preferably based on a plurality (preferably two or more) of compounds of the formula I, i.e. the proportion of these compounds is 5–95%, preferably 10–60% and particularly preferably in the range 20–50%.

The individual compounds of the formulae I to XVI and their sub-formulae which can be used in the media according to the invention are either known or can be prepared analogously to the known compounds.

Preferred embodiments are indicated below:

halogenated in the case of X in formula I means fluorinated and/or chlorinated, but preferably fluorinated X is preferably $OCF_3$, $OCF_2H$, $OC_2F_5$ or $OCH=CF_2$, or —O—Q—Y, in which Q is alkylene or alkenylene having 1 to 5 carbon atoms which is unsubstituted or monosubstituted or polysubstituted by fluorine and/or chlorine, and Y is Hal , $CHal_3$ or $CHHal_2$, and Hal is F or Cl, preferably F, Q is preferably —$CH_2$—, —$CH_2CH_2$—, —CHF—, —$CF_2$—, —$CH_2CHF$—, —$CHFCH_2$—, —$CH_2CHF$—, —$CF_2CH_2$—, —$CH_2$—$CH_2$—, —$CF_2CF_2$—, —$CH_2CF_2$—, —CH=CH—, —CH=CF—, —CF=CF—, —CH=CCl—, —$CH_2CH$=CF—, —$CH_2$—CF=CF— or —$CF_2$—CF=CF—, medium additionally contains one or more compounds selected from the group comprising the general formulae II to V:

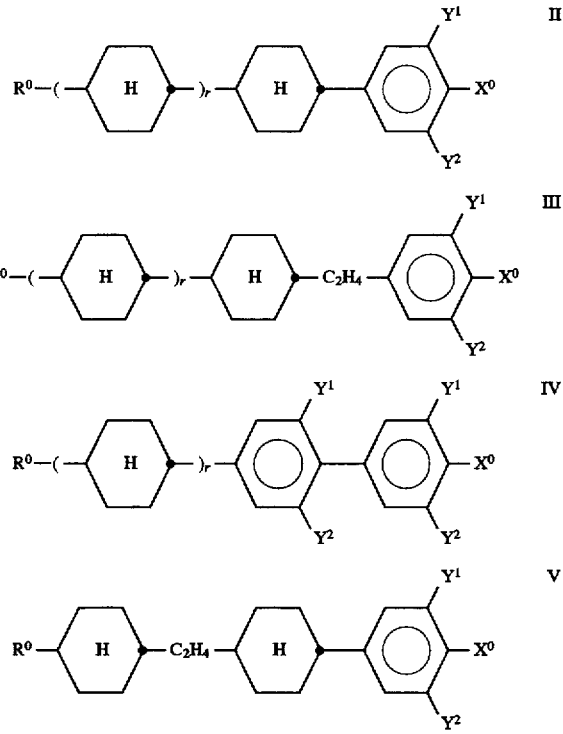

in which the individual radicals are as defined below:

$R^0$: alkyl, oxaalkyl, fluoroalkyl or alkenyl, in each case having up to 7 carbon atoms $X^0$: F, Cl, $CF_3$, $OCF_3$, $OCHF_2$, $OCH=CF_2$, $OCF=CF_2$, $OCFH$—$CF_2H$ or $OCF_2$—$CF_2H$ $Y^1$ and $Y^2$: each, independently of one another, H or F r: 0 or 1.

The compound of the formula IV is preferably

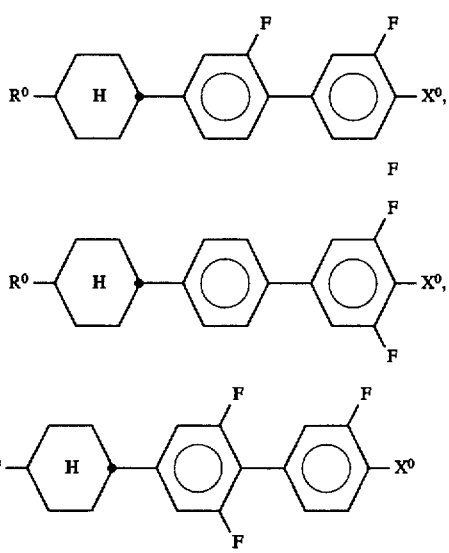

-continued

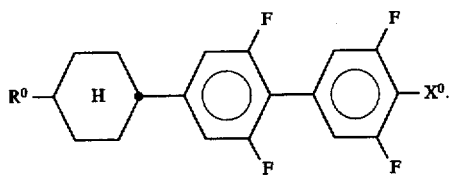

medium additionally contains one or more compounds selected from the group comprising the general formulae VI to XII:

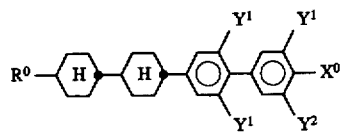 VI

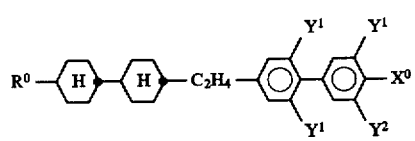 VII

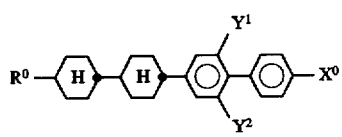 VIII

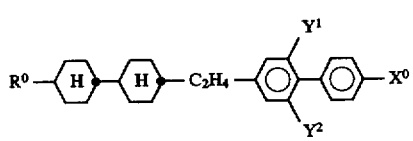 IX

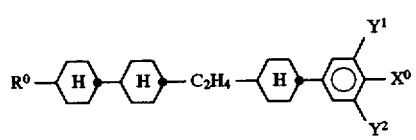 X

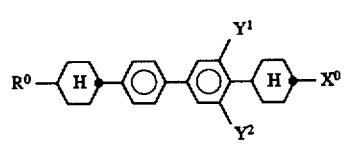 XI

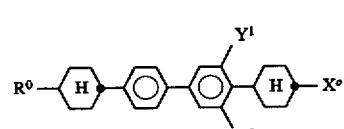 XII in which $R^0$, $Y^1$ and $Y^2$ are each, independently of one another, as defined on claim 2, and $X^0$ is F, Cl, $CF_3$, $OCF_3$, $OCHF_2$, alkyl, oxaalkyl, fluoroalkyl or alkenyl, in each case having up to 7 carbon atoms.

The proportion of compounds of the formulae I to V together is at least 50% by weight in the total mixture the proportion of compounds of the formula I is from 3 to 80% by weight in the total mixture the proportion of compounds of the formulae II to V is from 20 to 80% by weight in the total mixture

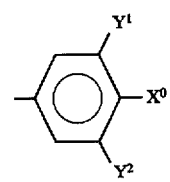

is preferably

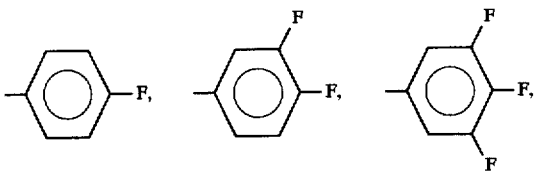

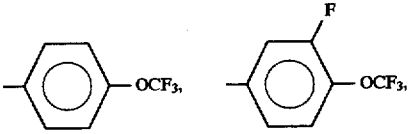

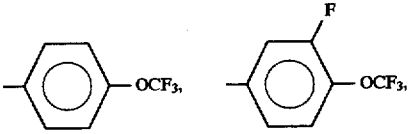

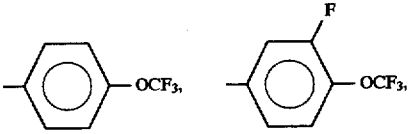

the medium contains compounds of the formulae II, III, IV or V $R^0$ is straight-chain alkyl or alkenyl having 2 to 7 carbon atoms the medium consists essentially of compounds of the formulae I to V the medium contains further compounds, preferably selected from the following group comprising the general formulae XIII to XVII:

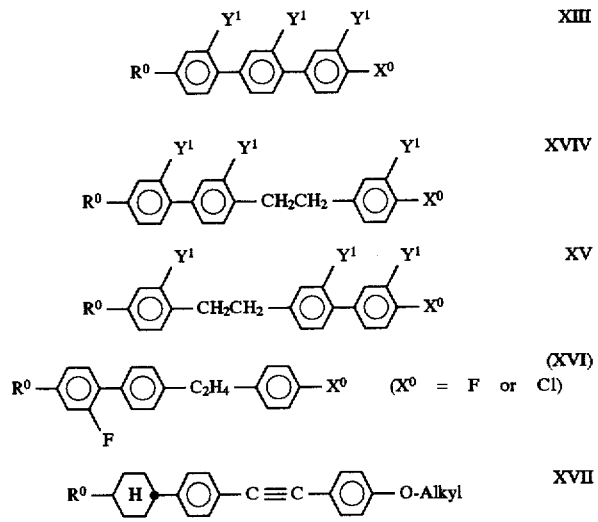

in which R⁰ and X⁰ are as defined in claim 2 and the 1,4-phenylene rings may be substituted by CN, chlorine or fluorine. The 1,4-phenylene rings are preferably mono- or polysubstituted by fluorine atoms.

the I: (II+III+IV+V) weight ratio is preferably from 1:10 to 10:1.

medium essentially comprises compounds selected from the group comprising the general formulae I to XII It has been found that even a relatively small proportion of compounds of the formula I mixed with conventional liquid-crystal materials, but in particular with one or more compounds of the formula II, III, IV and/or V, results in a significant lowering of the threshold voltage and in low values for the birefringence, and at the same time broad nematic phases with low smectic-nematic transition temperatures are observed, as a result of which the shelf life is improved. The compounds of the formulae I to V are colorless, stable and readily miscible with one another and with other liquid-crystal materials.

The term "alkyl" covers straight-chain and branched alkyl groups having 1–7 carbon atoms, in particular the straight-chain groups methyl, ethyl, propyl, butyl, pentyl, hexyl and heptyl. Groups having 2–5 carbon atoms are generally preferred.

The term "alkenyl" covers straight-chain and branched alkenyl groups having 2–7 carbon atoms, in particular the straight-chain groups. Preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups containing terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably 1 and m is preferably from 1 to 6.

Through a suitable choice of the meanings of R⁰ and X⁰, the addressing times, the threshold voltage, the gradient of the transmission characteristic lines, etc., can be modified as desired. For example, 1E-alkenyl radicals, 3E-alkenyl radicals, 2E-alkenyloxy radicals and the like generally give shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals.

A —$CH_2CH_2$— group in $Z^1$ generally results in higher values of $k_{33}/k_{11}$ compared with a simple covalent bond. Higher values of $k_{33}/k_{11}$ facilitate, for example, flatter transmission characteristic lines in TN cells with a 90° twist (for achieving grey tones) and steeper transmission characteristic lines in STN, SBE and OMI cells (greater multiplexing ability), and vice versa.

The optimum mixing ratio of the compounds of the formulae I and II+III+IV+V depends substantially on the desired properties, on the choice of the components of the formulae I, II, III, IV and/or V and on the choice of any other components which may be present. Suitable mixing ratios within the abovementioned range can easily be determined from case to case.

The total amount of compounds of the formulae I to XVI in the mixtures according to the invention is not crucial. The mixtures may therefore contain one or more further components in order to optimize various properties. However, the effect observed on the addressing times and the threshold voltage is generally greater the higher the total concentration of compounds of the formulae I to XI.

In a particularly preferred embodiment, the media according to the invention contain compounds of the formulae II to V (preferably II and/or III) in which X⁰ is $OCF_3$, $OCHF_2$, F, $OCH=CF_2$, $OCF=CF_2$ or $OCF_2$—$CF_2H$. A favorable synergistic effect with the compounds of the formula I results in particularly advantageous properties.

For STN applications, the media preferably contain compounds selected from the group comprising the formulae II to V in which X⁰ is preferably $OCHF_2$ or CN.

The media according to the invention may furthermore contain a component A comprising one or more compounds of the general formula I' having a dielectric anisotropy of from −1.5 to +1.5

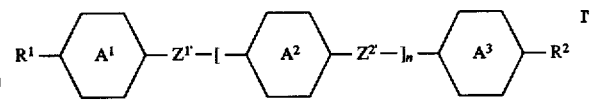

in which

R¹ and R² are each, independently of one another, n-alkyl, n-alkoxy, ω-fluoroalkyl or n-alkenyl having up to 9 carbon atoms,

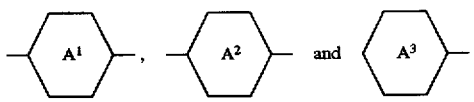

are each, independently of one another, 1,4-phenylene, 2- or 3-fluoro-1,4-phenylene, trans-1,4-cyclohexylene or 1,4-cyclohexenylene, $Z^{1'}$ and $Z^{2'}$ are each, independently of one another, —$CH_2CH_2$—, —C≡C—, —CO—O—, —O—CO— or a single bond, and n is 0, 1 or 2.

Component A preferably contains one or more compounds selected from the group comprising II1 to II7:

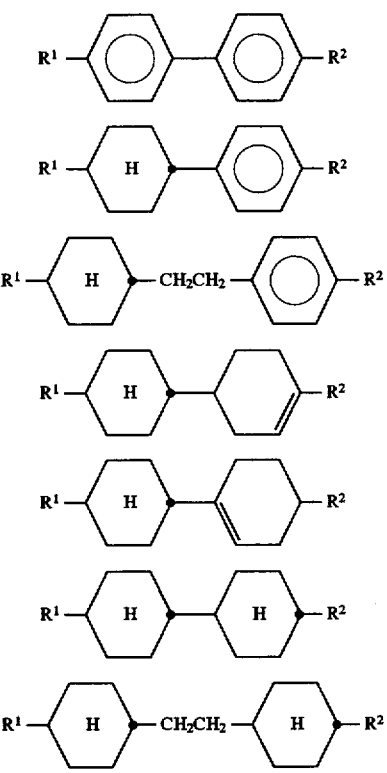

in which $R^1$ and $R^2$ are as defined under the formula I'.

Component A preferably additionally contains one or more compounds selected from the group comprising II8 to II20:

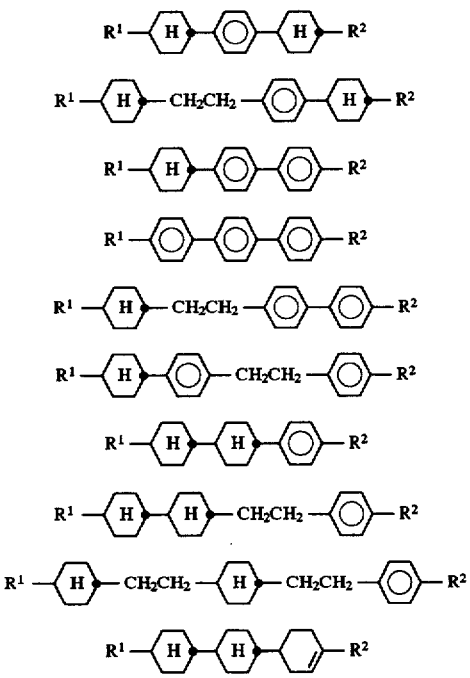

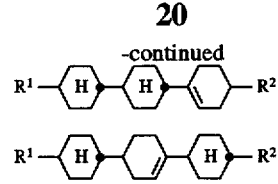

in which $R^1$ and $R^2$ are as defined under the formula I', and the 1,4-phenylene groups in II8 to II17 may each, independently of one another, also be monosubstituted or polysubstituted by fluorine.

Furthermore, component A preferably additionally contains one or more compounds selected from the group comprising II21 to II25:

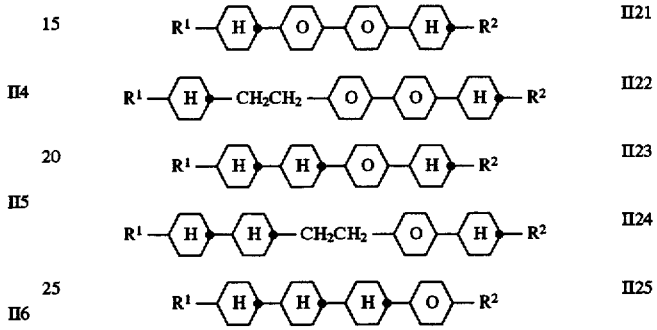

in which $R^1$ and $R^2$ are as defined under the formula I', and the 1,4-phenylene groups in II21 to II25 may also each, independently of one another, be monosubstituted or polysubstituted by fluorine.

Finally, preferred mixtures of this type are those in which component A contains one or more compounds selected from the group comprising II26 and II27:

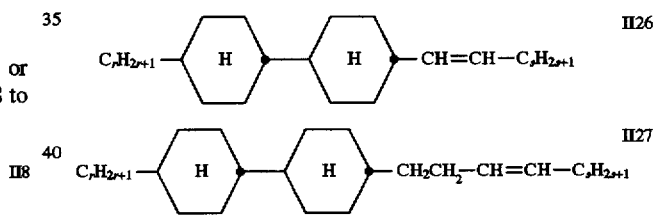

in which $C_sH_{2s+1}$ is a straight-chain alkyl group having up to 7 carbon atoms and s is 0, 1, 2 or 3.

In some cases, the addition of compounds of the formula

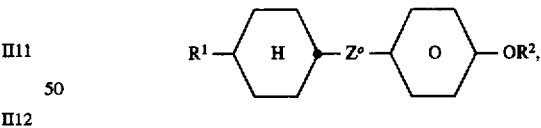

in which
  $R^1$ and $R^2$ are as defined under the formula I', and $Z^o$ is a single bond, —$C_2H_4$—

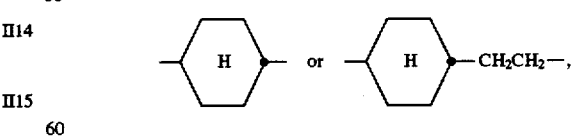

has proven advantageous for suppressing smectic phases, although this may reduce the specific resistance. In order to achieve parameter combinations which are ideal for the application, a person skilled in the art can easily determine whether and, if yes, in what amount these compounds may be added. Normally, less than 15%, in particular 5–10%, are used.

Preference is also given to liquid-crystal mixtures which contain one or more compounds selected from the group comprising III' and IV':

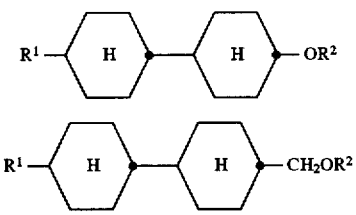

in which $R^1$ and $R^2$ are as defined under formula I'.

The type and amount of the polar compounds having positive dielectric anisotropy is not crucial per se. A person skilled in the art can use simple routine experiments to select suitable materials from the wide range of known and, in many cases, also commercially available components and base mixtures. The media according to the invention preferably contain one or more compounds of the formula I'''

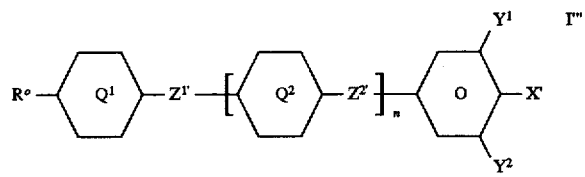

in which $Z^{1'}$, $Z^{2'}$ and n are as defined under the formula I'',

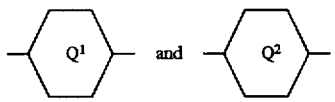

are each, independently of one another, 1,4-phenylene, trans-1,4-cyclohexylene or 3-fluoro-1,4-phenylene, and one of the radicals

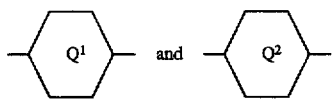

is alternatively trans-1,3-dioxane-2,5-diyl, pyrimidine-2,5-diyl, pyridine-2,5-diyl or 1,4-cyclohexenylene, $R^0$ is n-alkyl, n-alkenyl, n-alkoxy or n-oxaalkyl, in each case having up to 9 carbon atoms, $Y^1$ or $Y^2$ is H or F and X' is CN, halogen, $CF_3$, $OCF_3$ or $OCHF_2$.

In a preferred embodiment, the media according to the invention for STN or TN applications are based on compounds of the formula I'' in which X' is CN. It goes without saying that smaller or larger proportions of other compounds of the formula I'' (X' not being CN) are also possible. For MLC applications, the media according to the invention preferably contain only up to about 10% of nitriles of the formula I'' (but preferably no nitriles of the formula I'', but instead compounds of the formula I' where X' is halogen, $CF_3$, $OCF_3$ or $OCHF_2$). These media are preferably based on the compounds of the formulae II to XVI.

The media according to the invention preferably contain one or more compounds having a dielectric anisotropy in the range $-6 \leq \Delta\epsilon \leq -1.5$, of the formula I'''

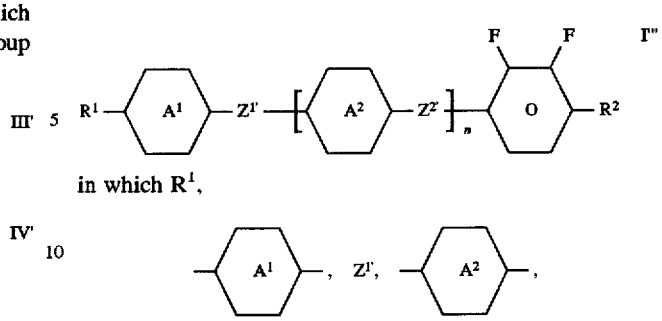

in which $R^1$, $Z^{2'}$, n and $R^2$ are as defined under formula I', for applications in which a small change in the capacity of the pixel on switching is desired (for example MIM displays or TFT displays).

Preference is given to compounds of the formulae $I^{1'''}$ to $I^{3'''}$:

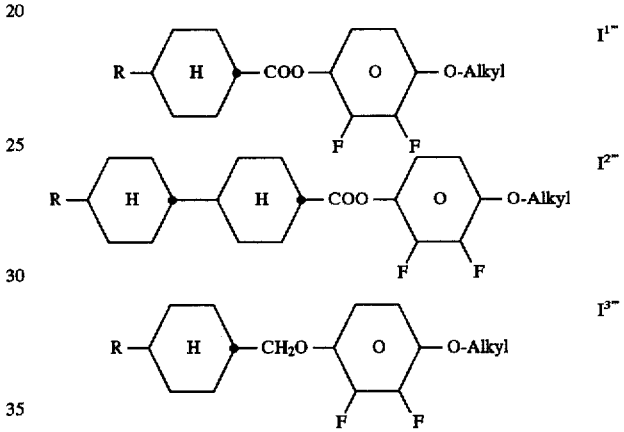

The construction of the STN and MLC displays according to the invention from polarizers, electrode base plates and electrodes with surface treatment corresponds to the construction which is conventional for displays of this type. The term conventional construction here is widely drawn and also covers all derivatives and modifications of the MLC display, in particular also matrix display elements based on poly-Si TFTs or MIMs.

An essential difference between the displays according to the invention and those customary hitherto based on the twisted nematic cell is, however, the choice of liquid-crystal parameters in the liquid-crystal layer.

The liquid-crystal mixtures which can be used according to the invention are prepared in a manner which is conventional per se. In general, the desired amount of the components used in the lesser amount is dissolved in the components making up the principal constituents, expediently at elevated temperature. It is also possible to mix solutions of the components in an organic solvent, for example in acetone, chloroform or methanol, and, after thorough mixing, to remove the solvent again, for example by distillation.

The dielectrics may also contain other additives known to those skilled in the art and described in the literature. For example, 0–15% of pleochroic dyes or chiral dopes can be added.

C denotes a crystalline phase, S a smectic phase, $S_B$ a smectic B phase, N a nematic phase and I the isotropic phase.

$V_{10}$ denotes the voltage for 10% transmission (view angle perpendicular to the plate surface). $t_{on}$ denotes the switch-on time and $t_{off}$ the switch-off time at an operating voltage corresponding to 2.5 times the value of $V_{10}$. $\Delta n$ denotes the optical anisotropy and no the refractive index. $\Delta\epsilon$ denotes the dielectric anisotropy ($\Delta\epsilon=\epsilon_{\parallel}-\epsilon_{\perp}$, where $\epsilon_{\parallel}$ is the dielectric constant parallel to the longitudinal molecular axes and $\epsilon_{\perp}$ is the dielectric constant perpendicular thereto). The electrooptical data were measured in a TN cell at the 1st minimum (i.e. at a d·Δn value of 0.5) at 20° C., unless expressly stated otherwise. The optical data were measured at 20° C., unless expressly stated otherwise.

In the present application and in the examples below, the structures of the liquid-crystal compounds are indicated by acronyms, with the transformation into chemical formulae taking place in accordance with Tables A and B below. All radicals $C_nH_{2n+1}$ and $C_mH_{2m+1}$ are straight-chain alkyl radicals containing n or m carbon atoms. The coding in Table B is self-evident. In Table A, only the acronym for the base structure is given. In individual cases, the acronym for the base structure is followed, separated by a hyphen, by a code for the substituents $R^1$, $R^2$, $L^1$ and $L^2$:

| Code for $R^1$ $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | COOC$_m$H$_{2m+1}$ | H | H |
| nOCCF$_2$.F.F | $C_nH_{2n+1}$ | OCH$_2$CF$_2$H | F | F |
| nOCF$_2$.F.F | $C_nH_{2n+1}$ | OCHF$_2$ | F | F |
| nCl.F.F | $C_nH_{2n+1}$ | Cl | F | F |
| nOCF$_3$.F.F | $C_nH_{2n+1}$ | OCF$_3$ | F | F |

TABLE A

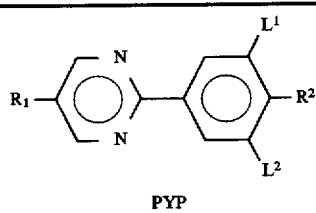

PYP

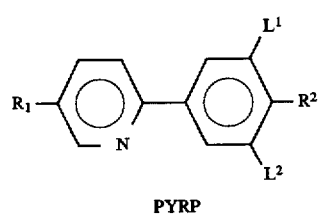

PYRP

TABLE A-continued

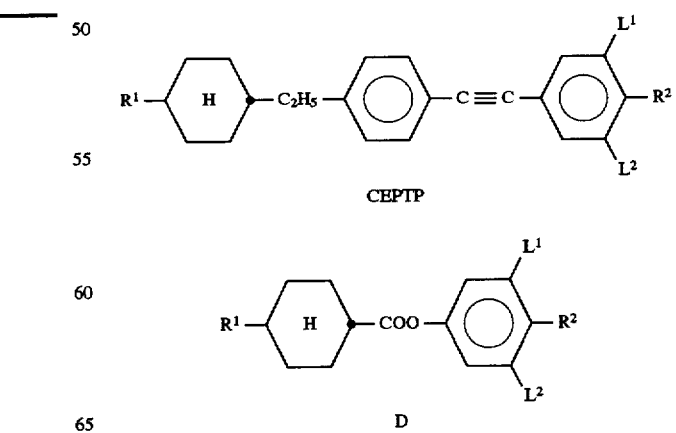

TABLE A-continued
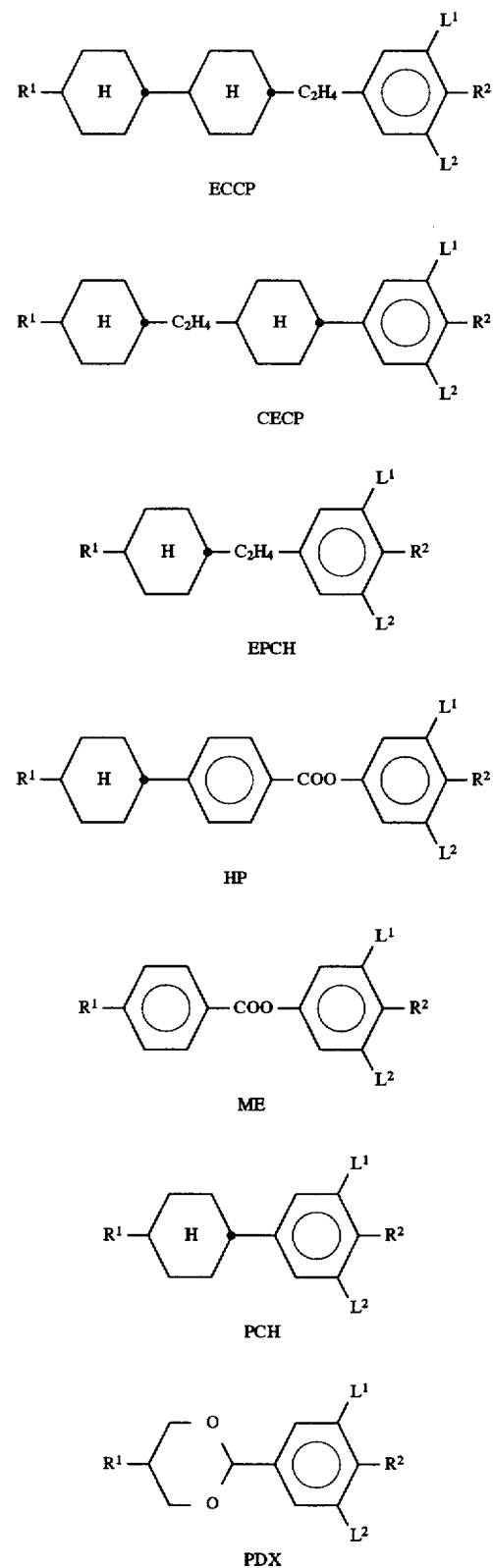
TABLE A-continued
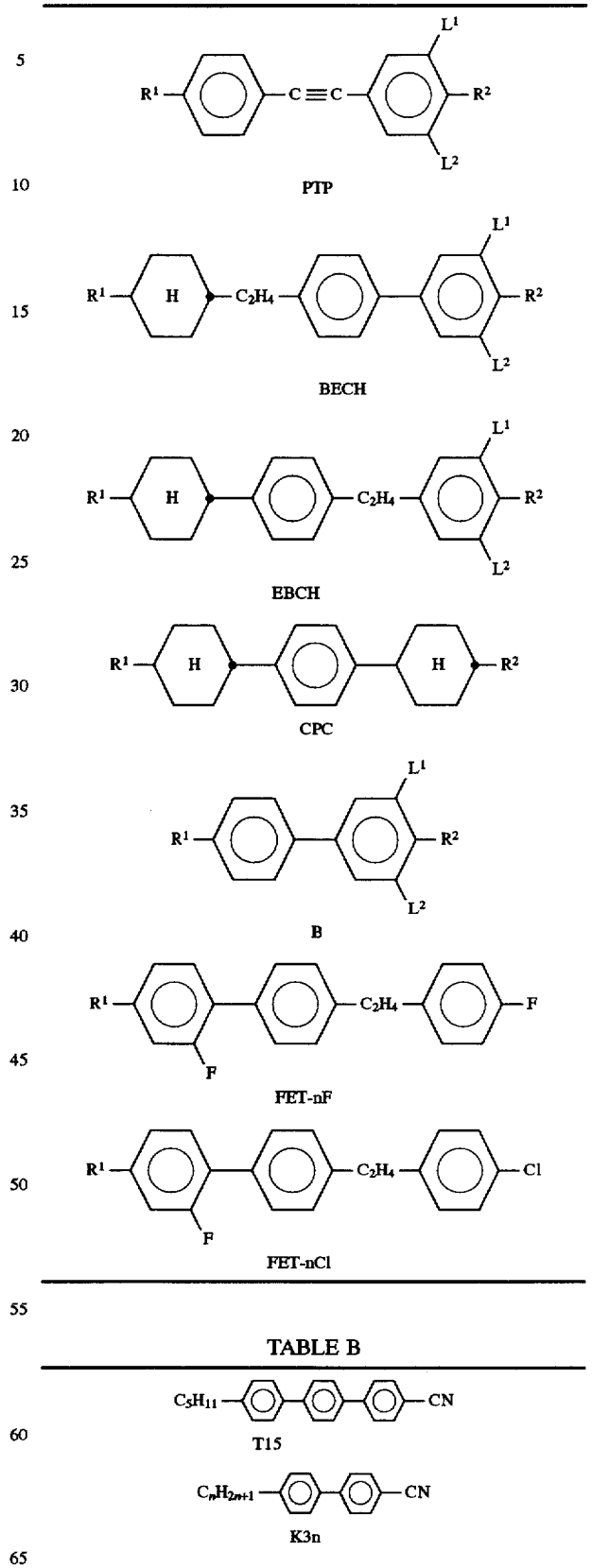
TABLE B
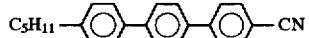

TABLE B-continued

- M3n: $C_nH_{2n+1}-O-\text{Ph}-\text{Ph}-CN$
- BCH-n.Fm: $C_nH_{2n+1}-\text{Cy}-\text{Ph(F)}-\text{Ph}-C_mH_{2m+1}$
- Inm: $C_nH_{2n+1}-\text{Cy}-C_2H_4-\text{Ph}-\text{Ph(F)}-C_mH_{2m+1}$
- C-nm: $C_nH_{2n+1}-\text{Cy}-\text{Cy}-OOC-C_mH_{2m+1}$
- C15: $C_2H_5-CH(CH_3)-CH_2-O-\text{Ph}-\text{Ph}-CN$
- CB15: $C_2H_5-CH(CH_3)-CH_2-\text{Ph}-\text{Ph}-CN$
- CBC-nmF: $C_nH_{2n+1}-\text{Cy}-\text{Ph}-\text{Ph(F)}-\text{Cy}-C_mH_{2m+1}$
- CCN-nm: $C_nH_{2n+1}-\text{Cy}-\text{Cy(CN)}-OOC-C_mH_{2m+1}$
- CCPC-nm: $C_nH_{2n+1}-\text{Cy}-\text{Cy}-COO-\text{Ph}-\text{Cy}-C_mH_{2m+1}$
- CH-nm: $C_nH_{2n+1}-\text{Cy}-\text{Cy}-COO-\text{Cy}-C_mH_{2m+1}$
- HD-nm: $C_nH_{2n+1}-\text{Cy}-\text{Ph}-OOC-\text{Cy}-C_mH_{2m+1}$
- HH-nm: $C_nH_{2n+1}-\text{Cy}-\text{Ph}-COO-\text{Cy}-C_mH_{2m+1}$
- NCB-nm: $C_nH_{2n+1}-\text{Ph}-\text{Ph}-\text{Cy(CN)}-C_mH_{2m+1}$
- OS-nm: $C_nH_{2n+1}-\text{Cy}-COO-\text{Cy}-C_mH_{2m+1}$
- CHE: $C_2H_5-\text{Cy}-COO-\text{Ph}-\text{Ph}-CN$

- ECBC-nm: $C_nH_{2n+1}-\text{Cy}-C_2H_4-\text{Ph}-\text{Ph}-\text{Cy}-C_mH_{2m+1}$
- ECCH-nm: $C_nH_{2n+1}-\text{Cy}-C_2H_4-\text{Cy}-\text{Ph}-C_mH_{2m+1}$
- CCH-n1Em: $C_nH_{2n+1}-\text{Cy}-\text{Cy}-CH_2O-C_mH_{2m+1}$
- T-nFm: $C_nH_{2n+1}-\text{Cy}-\text{Ph}-\text{Ph(F)}-\text{Ph}-C_mH_{2m+1}$
- ECCH-nm: $C_nH_{2n+1}-\text{Cy}-C_2H_4-\text{Cy}-\text{Cy}-C_mH_{2m+1}$
- CCH-n1Em: $C_nH_{2n+1}-\text{Cy}-\text{Cy}-CH_2OC_mH_{2m+1}$
- T-nFN: $C_nH_{2n+1}-\text{Ph}-\text{Ph(F)}-\text{Ph}-CN$
- CEUP-nX: $C_nH_{2n+1}-\text{Cy}-C_2H_4-\text{Ph(F,F)}-\text{Ph}-X$
- CEUP-nX.F: $C_nH_{2n+1}-\text{Cy}-C_2H_4-\text{Ph(F,F)}-\text{Ph(F)}-X$
- CUP-nX.F.F: $C_nH_{2n+1}-\text{Cy}-\text{Ph(F,F)}-\text{Ph(F,F)}-X$
- CCP-nOCCF2.F.F: $C_nH_{2n+1}-\text{Cy}-\text{Cy}-\text{Ph(F,F)}-OCH_2CF_2H$
- CCUP-nX: $C_nH_{2n+1}-\text{Cy}-\text{Cy}-\text{Ph(F)}-\text{Ph}-X$

TABLE B-continued

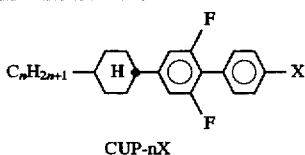

CUP-nX

The examples below are intended to illustrate the invention without representing a limitation. Above and below, percentages are by weight. All temperatures are given in degrees Celsius. m.p. denotes melting point, c.p.=clearing point. Furthermore, C=crystalline state, N=nematic phase, S=smectic phase and I=isotropic phase. The numbers between these symbols represent the transition temperatures. $\Delta n$ denotes optical anisotropy (589 nm, 20° C.) and the viscosity ($mm^2/sec$) was determined at 20° C.

"Conventional work-up" means that, if necessary, water is added, the mixture is extracted with dichloromethane, diethyl ether or toluene, the organic phase is separated off, dried and evaporated, and the product is purified by distillation under reduced pressure or crystallization and/or chromatography. The following abbreviations are used:

DMEU 1,3-dimethyl-2-imidazolidinone
POT potassium tertiary-butoxide
THF tetrahydrofuran
pTSOH p-toluenesulphonic acid

Example 1

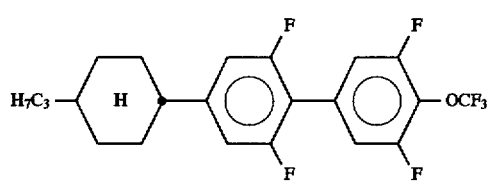

0.05 mol of 4-bromo-2,6-difluorotrifluoromethoxybenzene, 0.05 mol of 4-(trans-4-n-propylcyclohexyl)-2,6-difluorophenylboronic acid and 1 g of tetrakistriphenylphosphinepalladium(O) catalyst are dissolved in 100 ml of toluene and 40 ml of ethanol, and 50 ml of 2M $Na_2CO_3$ solution are added. The mixture is refluxed for 4 hours and worked up by extraction. Purification by chromatography and crystallization gives the target product: C 68 I; $\Delta\epsilon$=19.26; $\Delta n$=0.105.

The following compounds of the formula

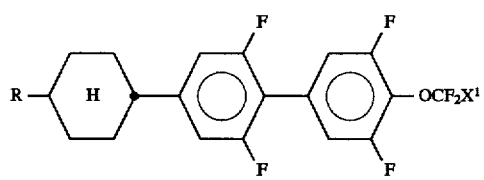

are prepared analogously

| R | L | $X^1$ |
|---|---|---|
| $H_3C$ | H | Cl |
| $H_3C$ | F | Cl |
| $H_5C_2$ | H | Cl |
| $H_5C_2$ | F | Cl |
| $H_7C_3$ | H | Cl |
| $H_7C_3$ | F | Cl |
| $H_9C_4$ | H | Cl |
| $H_9C_4$ | F | Cl |
| $H_{11}C_5$ | H | Cl |
| $H_{11}C_5$ | F | Cl |
| $H_{13}C_6$ | H | Cl |
| $H_{13}C_6$ | F | Cl |
| $H_{15}C_7$ | H | Cl |
| $H_{15}C_7$ | F | Cl |
| $H_3C$ | H | H |
| $H_3C$ | F | H |
| $H_5C_2$ | H | H |
| $H_5C_2$ | F | H |
| $H_7C_3$ | H | H |
| $H_7C_3$ | F | H |
| $H_9C_4$ | H | H |
| $H_9C_4$ | F | H |
| $H_{11}C_5$ | H | H |
| $H_{11}C_5$ | F | H |
| $H_{13}C_6$ | H | H |
| $H_{13}C_6$ | F | H |
| $H_{15}C_7$ | H | H |
| $H_{15}C_7$ | F | H |
| $H_3C$ | H | F |
| $H_3C$ | F | F |
| | | C 69 I; $\Delta n$ = +0.0857; $\Delta\epsilon$ = 19.33 |
| $H_5C_2$ | H | F |
| $H_5C_2$ | F | F |
| | | C 78 I; $\Delta n$ = +0.0878; $\Delta\epsilon$ = 18.86 |
| $H_7C_3$ | H | F |
| $H_9C_4$ | H | F |
| $H_9C_4$ | F | F |
| $H_{11}C_5$ | H | F |
| $H_{11}C_5$ | F | F |
| | | C 78 I; $\Delta n$ = +0,1014; $\Delta\epsilon$ = 18,74 |
| $H_{13}C_6$ | H | F |
| $H_{13}C_6$ | F | F |
| $H_{15}C_7$ | H | F |
| $H_{15}C_7$ | F | F |

Example 2

Step 2.1

Under a protective gas, 0.43 mol of sodium 4-bromo-2,6-difluorophenoxide are dissolved in 1000 ml of THF and cooled to −60° C. 0.44 mol of trifluoroacetyl chloride are introduced into the solution over the course of 0.5 h. The mixture is subsequently stirred at −60° C. for 1 h. The solution is allowed to warm to 10° C. and is evaporated. The residue is taken up in 1000 ml of hexane and stirred for 0.5 h. Finally, the solvent is removed on a rotary evaporator. After addition of 500 ml of dichloromethane, the product is subjected to conventional work-up.

Step 2.2

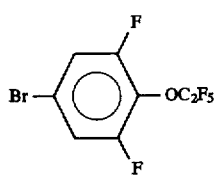

SF$_4$/HF is added to 0.05 mol of trifluoroacetate (step 2.1) analogously to I. L. Knunyants, G. G. Yakolson, Syntheses of Fluoroorganic Compounds, p. 267. The mixture is heated in an autoclave at 150° C. for 3 h and at 175° C. for 6 h. The mixture is then allowed to cool, and the gaseous products are passed into an alkali solution. After steam distillation, ether is added to the residue, and the product is then subjected to conventional work-up.

Step 2.3

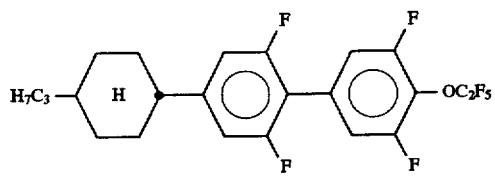

0.02 mol of pentafluoroethoxy-2,6-difluorobromobenzene are dissolved in 75 ml of THF in an N$_2$ atmosphere, and the mixture is warmed to 60° C. with stirring. A solution comprising 0.037 mol of potassium dihydrogenphosphate and 0.074 mol of sodium hydrogenphosphate in 40 ml of water and 0.46 g of tetrakis(triphenylphosphine) palladium (O) catalyst and 4-(trans-4-n-propylcyclohexyl)-2,6-difluorophenylboronic acid are added, and the mixture is refluxed for 24 h. The reaction mixture is allowed to cool to room temperature. After addition of methyl tert-butyl ether, the mixture is subjected to customary work-up. C 78 N (72.2) I; Δn=0.116; Δε=18.88.

The following compounds are prepared analogously:

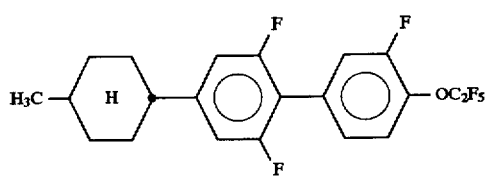

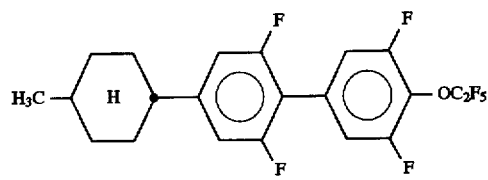

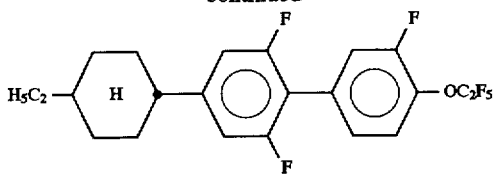

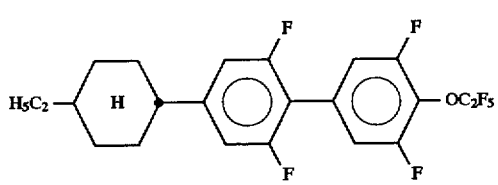

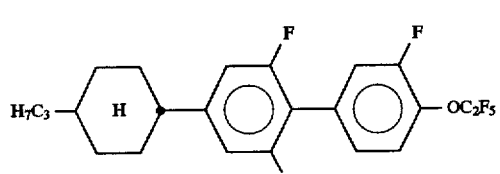

C 75 N 85,1 I; Δn = +0,124;
Δε = 15,51

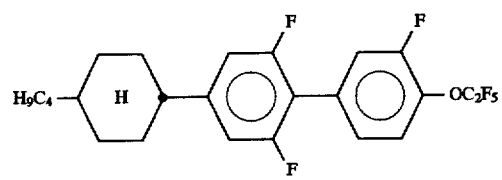

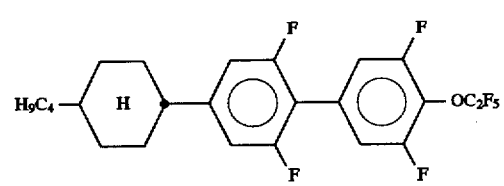

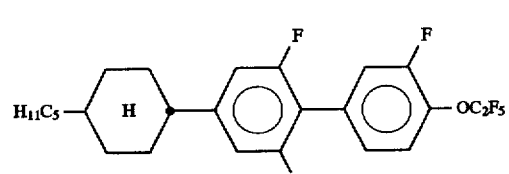

C 79 N 90,2 I; Δn = +0,125;
Δε = 15,04

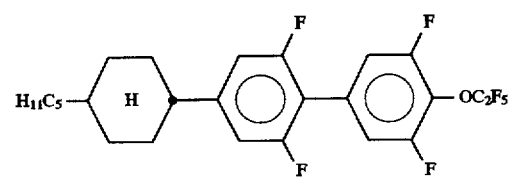

K 87 N 82,3 I; Δn = +0,117;
Δε = 18,32

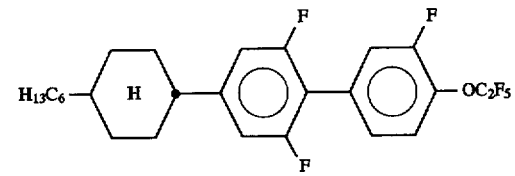

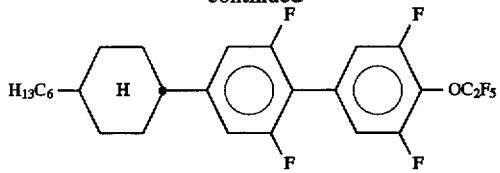

Mixture Examples

Example 1

| | | | |
|---|---|---|---|
| PCH—6F | 3.5% | Clearing point [°C.]: | 84 |
| PCH—7F | 3.0% | Viscocity at | 46 |
| CCP—2OCF$_2$.F.F | 16.0% | 20° C. [mm$^2$s$^{-1}$]: | |
| CCP—3OCF$_2$.F.F | 15.0% | Δn [20° C., 589 nm]: | 0.1017 |
| CCP—5OCF$_2$.F.F | 16.0% | V$_{(10,0,20)}$ [V]: | 1.16 |
| CUP—2F.F | 6.0% | V$_{(50,0,20)}$ [V]: | 1.45 |
| CUP—3F.F | 6.0% | V$_{(90,0,20)}$ [V]: | 1.82 |
| CUP—5F.F | 5.0% | | |
| CUP—2OCF$_2$.F.F | 6.0% | | |
| CUP—3OCF$_2$.F.F | 6.0% | | |
| CUP—5OCF$_2$.F.F | 6.0% | | |
| CBC—33F | 3.5% | | |
| CBC—53F | 4.0% | | |
| CBC—55F | 4.0% | | |

Example 2

| | | | |
|---|---|---|---|
| PCH—5F | 3.0% | S → N [°C.]: | |
| CCP—2OCF$_2$.F.F | 16.0% | Clearing point [°C.]: | +103 |
| CCP—3OCF$_2$.F.F | 15.0% | Δn [589 nm, 20° C.]: | +0.1086 |
| CCP—5OCF$_2$.F.F | 16.0% | V$_{(10,0,20)}$ [V]: | 1.26 |
| CUP—2F.F | 5.0% | V$_{(90,0,20)}$ [V]: | 2.04 |
| CUP—3F.F | 5.0% | | |
| CUP—5F.F | 5.0% | | |
| CUP—3OCF$_2$.F.F | 10.0% | | |
| CUP—5OCF$_2$.F.F | 10.0% | | |
| CBC—33F | 5.0% | | |
| CBC—53F | 5.0% | | |
| CBC—55F | 5.0% | | |

Example 3

| | | | |
|---|---|---|---|
| PCH—5F | 3.0% | S → N [°C.]: | |
| CCP—2OCF$_2$.F.F | 16.0% | Clearing point [°C.]: | +100 |
| CCP—3OCF$_2$.F.F | 15.0% | Δn [589 nm, 20° C.]: | +0.1077 |
| CCP—5OCF$_2$.F.F | 16.0% | Δε [1 kHz, 20° C.]: | |
| CUP—2F.F | 6.0% | V$_{(10,0,20)}$ [V]: | 1.23 |
| CUP—3F.F | 6.0% | V$_{(90,0,20)}$ [V]: | 1.95 |
| CUP—5F.F. | 5.0% | | |
| CUP—2OCF$_2$.F.F | 6.0% | | |
| CUP—3OCF$_2$.F.F | 6.0% | | |
| CUP—5OCF$_2$.F.F | 6.0% | | |
| CBC—33F | 5.0% | | |
| CBC—53F | 5.0% | | |
| CBC—55F | 5.0% | | |

Example 4

| | | | |
|---|---|---|---|
| PCH—6F | 4,0% | Clearing point [°C.] | +78 |
| PCH—7F | 4,0% | | |
| CCP—2OCF$_2$.F.F | 16,0% | | |
| CCP—3OCF$_2$.F.F | 15,0% | | |
| CCP—5OCF$_2$.F.F | 16,0% | | |
| CUP—2F.F | 6,0% | | |
| CUP—3F.F | 6,0% | | |
| CUP—5F.F | 5,0% | | |
| CUP—2OCF$_2$.F.F | 6,0% | | |
| CUP—3OCF$_2$.F.F | 6,0% | | |
| CUP—5OCF$_2$.F.F | 6,0% | | |
| CBC—33F | 3,0% | | |
| CBC—53F | 3,0% | | |
| CBC—55F | 4,0% | | |

Example 5

| | | | |
|---|---|---|---|
| PCH—6F | 3,5% | S → N [°C.]: | <−40 |
| PCH—7F | 3,0% | Clearing point [°C.]: | +84 |
| CCP—2OCF$_2$.F.F | 16,0% | Δn [589 nm, 20°]C.]: | 0,1017 |
| CCP—3OCF$_2$.F.F | 15,0% | Δε [1 kHz, 20° C.]: | |
| CCP—5OCF$_2$.F.F | 16,0% | V$_{(10,0,20)}$ [V]: | 1,24 |
| CUP—2F.F | 6,0% | V$_{(90,0,20)}$ [V]: | 2,01 |
| CUP—3F.F | 6,0% | v 20: | 50 cSt |
| CUP—5F.F | 5,0% | v −30: | 4630 cSt |
| CUP—2OCF$_2$.F.F | 6,0% | HR (100°): | 91% |
| CUP—3OCF$_2$.F.F | 6,0% | | |
| CUP—5OCF$_2$.F.F | 6,0% | | |
| CBC—33F | 3,5% | | |
| CBC—53F | 4,0% | | |
| CBC—55F | 4,0% | | |

Example 6

| | | | |
|---|---|---|---|
| PCH—5F | 3,0% | S → N [°C.]: | |
| CCP—2OCF$_2$.F.F | 16,0% | Clearing point [°C.]: | +109 |
| CCP—3OCF$_2$.F.F | 15,0% | Δn [589 nm, 20° C.]: | +0,0998 |
| CCP—5OCF$_2$.F.F | 16,0% | Δε [1 kHz, 20° C.]: | |
| CUP—2F.F | 6,0% | V$_{(10,0,20)}$ [V]: | 1,27 |
| CUP—3F.F | 6,0% | V$_{(90,0,20)}$ [V]: | 2,01 |
| CUP—5F.F | 5,0% | | |
| CUP—2OCF$_2$.F.F | 6,0% | | |
| CUP—3OCF$_2$.F.F | 6,0% | | |
| CUP—5OCF$_2$.F.F | 6,0% | | |
| CBC—33F | 5,0% | | |
| CBC—34F | 5,0% | | |
| CBC—35F | 5,0% | | |

Example 7

| | | | |
|---|---|---|---|
| PCH—5F | 3,0% | S → N [°C.]: | |
| CCP—2OCF$_2$.F.F | 16,0% | Clearing point [°C.]: | +97 |
| CCP—3OCF$_2$.F.F | 15,0% | Δn [589 nm, 20° C.]: | +0,1050 |
| CCP—5OCF$_2$.F.F | 16,0% | Δε [1 kHz, 20° C.]: | |
| CUP—2F.F | 5,0% | V$_{(10,0,20)}$ [V]: | 1,15 |
| CUP—3F.F | 5,0% | V$_{(90,0,20)}$ [V]: | 1,82 |
| CUP—5F.F | 5,0% | | |
| CUP—3OCF$_3$.F.F | 10,0% | | |
| CUP—5OCF$_3$.F.F | 10,0% | | |
| CBC—33F | 5,0% | | |
| CBC—53F | 5,0% | | |
| CBC—55F | 5,0% | | |

Example 8

| | | | |
|---|---|---|---|
| PCH—5F | 3,0% | S → N [°C.]: | |
| CCP—2OCF$_2$.F.F | 16,0% | Clearing point [°C.]: | +103 |
| CCP—3OCF$_2$.F.F | 15,0% | Δn [589 nm, 20° C.]: | +0,1075 |
| CCP—5OCF$_2$.F.F | 16,0% | Δε [1 kHz 20° C.]: | |
| CUP—2F.F | 5,0% | V$_{(10,0,20)}$ [V]: | 1,27 |
| CUP—3F.F | 5,0% | V$_{(90,0,20)}$ [V]: | 2,02 |
| CUP—5F.F | 5,0% | | |
| CUP—3OCF$_3$.F.F | 10,0% | | |
| CUP—5OCF$_3$.F.F | 10,0% | | |
| CBC—33F | 5,0% | | |
| CBC—53F | 5,0% | | |
| CBC—55F | 5,0% | | |

Example 9

| | | | |
|---|---|---|---|
| PCH—5F | 3,0% | S → N [°C.]: | |
| CCP—2OCF$_2$.F.F | 16,0% | Clearing point [°C.]: | +100 |
| CCP—3OCF$_2$.F.F | 15,0% | Δn [589 nm, 20°]C.]: | +0,1068 |
| CCP—5OCF$_2$.F.F | 16,0% | Δε [1 kHz, 20° C.]: | |
| CUP—2F.F | 6,0% | V$_{(10,0,20)}$ [V]: | 1,27 |
| CUP—3F.F | 6,0% | V$_{(90,0,20)}$ [V]: | 1,99 |
| CUP—5F.F | 5,0% | | |
| CUP—2OCF$_3$.F.F | 6,0% | | |
| CUP—3OCF$_3$.F.F | 6,0% | | |
| CUP—5OCF$_3$.F.F | 6,0% | | |
| CBC—33F | 5,0% | | |
| CBC—53F | 5,0% | | |
| CBC—55F | 5,0% | | |

Example 10

| | | | |
|---|---|---|---|
| PCH—6F | 4,0% | S → N [°C.]: | |
| PCH—7F | 4,0% | Clearing point [°C.]: | +77 |
| CCP—2OCF$_2$.F.F | 16,0% | Δn [589 nm, 20° C.]: | 0,0980 |
| CCP—3OCF$_2$.F.F | 15,0% | Δε [1 kHz, 20° C.]: | |
| CCP—5OCF$_2$.F.F | 16,0% | V$_{(10,0,20)}$ [V]: | |
| CUP—2F.F | 6,0% | V$_{(90,0,20)}$ [V]: | |
| CUP—3F.F | 6,0% | | |
| CUP—5F.F | 5,0% | | |
| CUP—2OCF$_2$.F.F | 6,0% | | |
| CUP—3OCF$_3$.F.F | 6,0% | | |

-continued

| | | | |
|---|---|---|---|
| CUP—5OCF₃.F.F | 6,0% | | |
| CBC—33F | 4,0% | | |
| CBC—53F | 3,0% | | |
| CBC—55F | 3,0% | | |
| Example 11 | | | |
| PCH—6F | 6,0% | S → N [°C]: | |
| CCP—2OCF₂.F.F | 16,0% | Clearing point [°C]: | +85 |
| CCP—3OCF₂.F.F | 15,0% | Δn [589 nm, 20° C.]: | +0,1015 |
| CCP—5OCF₂.F.F | 16,0% | Δε [1 kHz, 20° C.]: | |
| CUP—2F.F | 6,0% | $V_{(10,0,20)}$ [V]: | 1,16 |
| CUP—3F.F | 6,0% | $V_{(90,0,20)}$ [V]: | 1,83 |
| CUP—5F.F | 5,0% | | |
| CUP—2OCF₃.F.F | 6,0% | | |
| CUP—3OCF₃.F.F | 6,0% | | |
| CUP—5OCF₃.F.F | 6,0% | | |
| CBC—33F | 4,0% | | |
| CBC—53F | 4,0% | | |
| CBC—55F | 4,0% | | |
| Example 12 | | | |
| PCH—6F | 3,5% | S → N [°C]: | |
| PCH—7F | 3,0% | Clearing point [°C]: | |
| CCP—2OCF₂.F.F | 12,0% | Δn (589 nm, 20° C.]: | |
| CCP—3OCF₂.F.F | 12,0% | Δε [1 kHz, 20° C.]: | |
| CCP—5OCF₂.F.F | 12,0% | $V_{(10,0,20)}$ [V]: | |
| CUP—2F.F | 5,0% | $V_{(90,0,20)}$ [V] | |
| CUP—3F.F | 5,0% | | |
| CUP—5F.F | 5,0% | | |
| CUP—2OCF₃.F.F | 5,0% | | |
| CUP—3OCF₃.F.F | 5,0% | | |
| CUP—5OCF₃.F.F | 5,0% | | |
| CUP—3OCCF₂.F.F | 8,0% | | |
| CUP—5OCCF₂.F.F | 8,0% | | |
| CBC—33F | 3,5% | | |
| CBC—53F | 4,0% | | |
| CBC—55F | 4,0% | | |
| Example 13 | | | |
| PCH—5F | 5,0% | S → N [°C]: | +83 |
| PCH—7F | 6,0% | Clearing point [°C]: | +0,0882 |
| CCP—2OCF₃ | 11,0% | Δn [589 nm, 20° C.]: | |
| CCP—3OCF₃ | 12,0% | Δε [1 kHz, 20° C.]: | |
| CCP—4OCF₃ | 10,0% | $V_{(10,0,20)}$ [V]: | 1,40 |
| CCP—5OCF₃ | 12,0% | $V_{(90,0,20)}$ [V]: | 2,18 |
| CUP—3OCF₃.F.F | 12,0% | | |
| BCH—5F.F.F | 11,0% | | |
| CCP—3F.F.F | 12,0% | | |
| CCP—5F.F.F | 9,0% | | |
| Example 14 | | | |
| PCH—5F | 9,0% | | |
| PCH—6F | 7,2% | | |
| PCH—7F | 5,4% | | |
| CCP—2OCF₃ | 7,2% | | |
| CCP—3OCF₃ | 10,8% | | |
| CCP—4OCF₃ | 6,3% | | |
| CCP—5OCF₃ | 9,9% | | |
| BCH—3F.F | 10,8% | | |
| BCH—5F.F | 9,0% | | |
| ECCP—3OCF₃ | 4,5% | | |
| ECCP—5OCF₃ | 4,5% | | |
| CBC—33F | 1,8% | | |
| CBC—53F | 1,8% | | |
| CBC—55F | 1,8% | | |
| CUP—3OCF₃.F.F | 10,0% | | |
| Example 15 | | | |
| PCH—5F | 5,0% | S → N (°C]: | <−20 |
| PCH—7F | 6,0% | Clearing point [°C]: | +80 |
| CCP—2OCF₃ | 11,0% | Δn [589 nm, 20° C.]: | +0,0858 |
| CCP—3OCF₃ | 12,0% | $V_{(10,0,20)}$ [V]: | 1,36 |
| CCP—4OCF₃ | 10,0% | $V_{(90,0,20)}$ [V]: | 2.15 |
| CCP—5OCF₃ | 12,0% | | |
| CUP—3OCF₃.F.F | 12,0% | | |
| CUP—5OCF₃.F.F | 11,0% | | |
| CCP—3F.F.F | 12,0% | | |
| CCP—3F.F.F | 9,0% | | |

-continued

| | | | |
|---|---|---|---|
| Example 16 | | | |
| PCH—5F | 3,0% | S → N [°C]: | <−30 |
| CCP—2OCF₂.F.F | 16,0% | Clearing point [°C]: | +101 |
| CCP—3OCF₂.F.F | 15,0% | Δn [589 nm, 20° C.]: | +0,1071 |
| CCP—5OCF₂.F.F | 16,0% | $V_{(10,0,20)}$ [V]: | 1,23 |
| CUP—2F.F | 5,0% | $V_{(90,0,20)}$ [V]: | 1,94 |
| CUP—3F.F | 5,0% | | |
| CUP—5F.F | 5,0% | | |
| CUP—3OCF₃.F.F | 10,0% | | |
| CUP—5OCF₃.F.F | 10,0% | | |
| CBC—33F | 5,0% | | |
| CBC—53F | 5,0% | | |
| CBC—55F | 5,0% | | |
| Example 17 | | | |
| PCH—5F | 8,5% | | |
| PCH—6F | 6,8% | | |
| PCH—7F | 5,1% | | |
| CCP—2OCF₃ | 6,8% | | |
| CCP—3OCF₃ | 10,2% | | |
| CCP—4OCF₃ | 6,0% | | |
| CCP—5OCF₃ | 9,3% | | |
| BCH—3F.F | 10,2% | | |
| BCH—5F.F | 8,5% | | |
| ECCP—3OCF₃ | 4,2% | | |
| ECCP—5OCF₃ | 4,2% | | |
| CBC—33F | 1,7% | | |
| CBC—53F | 1,7% | | |
| CBC—55F | 1,7% | | |
| CUP—3OCF₃.F.F | 15,0% | | |
| Example 18 | | | |
| PCH—5F | 8,0% | Clearing point [°C]: | 75,6 |
| PCH—6F | 6,4% | | |
| PCH—7F | 4,8% | | |
| CCP—2OCF₃ | 6,4% | | |
| CCP—3OCF₃ | 9,6% | | |
| CCP—4OCF₃ | 5,6% | | |
| CCP—5OCF₃ | 8,8% | | |
| BCH—3F.F | 9,6% | | |
| BCH—5F.F | 8,0% | | |
| ECCP—3OCF₃ | 4,0% | | |
| ECCP—5OCF₃ | 4,0% | | |
| CBC—33F | 1,6% | | |
| CBC—53F | 1,6% | | |
| CBC—55F | 1,6% | | |
| CUP—3OCF₃.F.F | 20,0% | | |
| Example 19 | | | |
| PCH—6F | 1,0% | Clearing point [°C]: | +74 |
| CCP—2OCF₂.F.F | 17,0% | Δn [589 nm, 20° C.]: | +0,0994 |
| CCP—3OCF₂.F.F | 17,0% | $V_{(10,0,20)}$ [V]: | 1,00 |
| CCP—5OCF₂.F.F | 17,0% | $V_{(90,0,20)}$ [V]: | 1,59 |
| CUP—2F.F | 7,0% | | |
| CUP—3F.F | 7,0% | | |
| CUP—5F.F | 8,0% | | |
| CUP—3OCF₃.F.F | 11,0% | | |
| CUP—5OCF₃.F.F | 11,0% | | |
| CBC—53F | 2,0% | | |
| CBC—55F | 2,0% | | |
| Example 20 | | | |
| PCH—6F | 1,0% | Clearing point [°C.) : | +83 |
| CCP—2OCF₂.F.F | 16,0% | Δn [589 nm, 20° C.]: | +0,1025 |
| CCP—3OCF₂.F.F | 17,0% | $V_{(10,0,20)}$ [V]: | 1,11 |
| CCP—5OCF₂.F.F | 17,0% | $V_{(90,0,20)}$ [V]: | 1,80 |
| CUP—2F.F | 6,0% | | |
| CUP—3F.F | 7,0% | | |
| CUP—5F.F | 8,0% | | |
| CUP—3OCF₃.F.F | 10,0% | | |
| CUP—5OCF₃.F.F | 11,0% | | |
| CBC—53F | 3,0% | | |
| CBC—55F | 4,0% | | |
| Example 21 | | | |
| CCP—2OCF₂.F.F | 16,0% | Clearing point [°C]: | 86 |
| CCP—3OCF₂.F.F | 16,0% | Δn [589 nm, 20° C.]: | +0,1046 |
| CCP—5OCF₂.F.F | 17,0% | $V_{(10,0,20)}$ [V]: | 1,10 |
| CUP—2F.F | 6,0% | $V_{(90,0,20)}$ [V]: | 1,76 |

-continued

| | | | |
|---|---|---|---|
| CUP—3F.F | 7,0% | | |
| CUP—5F.F | 8,0% | | |
| CUP—3OCF$_3$.F.F | 11,0% | | |
| CUP—5OCF$_3$.F.F | 11,0% | | |
| CBC—53F | 4,0% | | |
| CBC—55F | 4,0% | | |

Example 22

| | | | |
|---|---|---|---|
| PCH—5F | 9,0% | Clearing point [°C.]: | 80,6 |
| PCH—6F | 7,2% | Δn [589 nm, 20° C.]: | 0,0954 |
| PCH—7F | 5,4% | Δε [1 kHz, 20° C.]: | 6,67 |
| CCP—2OCF$_3$ | 7,2% | | |
| CCP—3OCF$_3$ | 10,8% | | |
| CCP—4OCF$_3$ | 8,1% | | |
| CCP—5OCF$_3$ | 8,1% | | |
| BCH—3F.F | 10,8% | | |
| BCH—5F.F | 9,0% | | |
| ECCP—3OCF$_3$ | 4,5% | | |
| ECCP—5OCF$_3$ | 4,5% | | |
| CBC—33F | 1,8% | | |
| CBC—53F | 1,8% | | |
| CBC—55F | 1,8% | | |
| CUP—1OCF$_3$.F.F | 10,0% | | |

Example 23

| | | | |
|---|---|---|---|
| PCH—5F | 9,0% | Clearing point [°C.]: | 81,8 |
| PCH—6F | 7,2% | Δn [589 nm, 20° C.]: | 0,0956 |
| PCH—7F | 5,4% | Δε [1 kHz, 20° C.]: | 6,59 |
| CCP—2OCF$_3$ | 7,2% | | |
| CCP—3OCF$_3$ | 10,8% | | |
| CCP—4OCF$_3$ | 8,1% | | |
| CCP—5OCF$_3$ | 8,1% | | |
| BCH—3F.F | 10,8% | | |
| BCH—5F.F | 9,0% | | |
| ECCP—3OCF$_3$ | 4,5% | | |
| ECCP—5OCF$_3$ | 4,5% | | |
| CBC—33F | 1,8% | | |
| CBC—53F | 1,8% | | |
| CBC—55F | 1,8% | | |
| CUP—2OCF$_3$.F.F | 10,0% | | |

Example 24

| | | | |
|---|---|---|---|
| PCH—5F | 9,0% | Clearing point [°C.]: | 84,5 |
| PCH—6F | 7,2% | Δn [589 nm, 20° C.]: | 0,0974 |
| PCH—7F | 5,4% | Δε [1 kHz, 20° C.]: | 6,68 |
| CCP—2OCF$_3$ | 7,2% | | |
| CCP—3OCF$_3$ | 10,8% | | |
| CCP—4OCF$_3$ | 8,1% | | |
| CCP—5OCF$_3$ | 8,1% | | |
| BCH—3F.F | 10,8% | | |
| BCH—5F.F | 9,0% | | |
| ECCP—3OCF$_3$ | 4,5% | | |
| ECCP—5OCF$_3$ | 4,5% | | |
| CBC—33F | 1,8% | | |
| CBC—53F | 1,8% | | |
| CBC—55F | 1,8% | | |
| CUP—3OCF$_3$.F.F | 10,0% | | |

Example 25

| | | | |
|---|---|---|---|
| PCH—5F | 9,0% | Clearing point [°C.]: | 85,2 |
| PCH—6F | 7,2% | Δn [589 nm, 20° C.]: | 0,0970 |
| PCH—7F | 5,4% | Δε [1 kHz, 20° C.]: | 6,60 |
| CCP—2OCF$_3$ | 7,2% | | |
| CCP—3OCF$_3$ | 10,8% | | |
| CCP—4OCF$_3$ | 8,1% | | |
| CCP—5OCF$_3$ | 8,1% | | |
| BCH—3F.F | 10,8% | | |
| BCH—5F.F | 9,0% | | |
| ECCP—3OCF$_3$ | 4,5% | | |
| ECCP—5OCF$_3$ | 4,5% | | |
| CBC—33F | 1,8% | | |
| CBC—53F | 1,8% | | |
| CBC—55F | 1,8% | | |
| CUP—5OCF$_3$.F.F | 10,0% | | |

Example 26

| | | | |
|---|---|---|---|
| PCH—5F | 5,0% | Clearing point [°C.]: | +81 |
| PCH—7F | 6,0% | Δn [589 nm, 20° C.]: | 0,0884 |
| CCP—2OCF$_3$ | 11,0% | V$_{(10,0,20)}$ [V]: | 1,42 |
| CCP—3OCF$_3$ | 12,0% | V$_{(90,0,20)}$ [V]: | 2,22 |

-continued

| | | | |
|---|---|---|---|
| CCP—4OCF$_3$ | 10,0% | | |
| CCP—5OCF$_3$ | 12,0% | | |
| CUP—2OCF$_2$.F.F | 12,0% | | |
| BCH—5F.F.F | 11,0% | | |
| CCP—3F.F.F | 12,0% | | |
| CCP—5F.F.F | 9,0% | | |

Example 27

| | | | |
|---|---|---|---|
| PCH—5F | 5,0% | Clearing point [°C.]: | +84 |
| PCH—7F | 6,0% | Δn [589 nm, 20° C.]: | 0,0903 |
| CCP—2OCF$_3$ | 11,0% | V$_{(10,0,20)}$ [V]: | 1,45 |
| CCP—3OCF$_3$ | 12,0% | V$_{(90,0,20)}$ [V]: | 2,30 |
| CCP—4OCF$_3$ | 10,0% | | |
| CCP—5OCF$_3$ | 12,0% | | |
| CUP—3CCF2.F.F | 12,0% | | |
| BCH—5F.F.F | 11,0% | | |
| CCP—3F.F.F | 12,0% | | |
| CCP—5F.F.F | 9,0% | | |

Example 28

| | | | |
|---|---|---|---|
| PCH—5F | 5,0% | Clearing point [°C.]: | +83 |
| PCH—7F | 6,0% | Δn [589 nm, 20° C.]: | 0,0908 |
| CCP—2OCF$_3$ | 11,0% | V$_{(10,0,20)}$ [V]: | 1,46 |
| CCP—3OCF$_3$ | 12,0% | V$_{(90,0,20)}$ [V]: | 2,27 |
| CCP—4OCF$_3$ | 10,0% | | |
| CCP—5OCF$_3$ | 12,0% | | |
| BCH—3F.F.F | 12,0% | | |
| CUP—5OCF$_2$.F.F | 11,0% | | |
| CCP—3F.F.F | 12,0% | | |
| CCP—5F.F.F | 9,0% | | |

Example 29

| | | | |
|---|---|---|---|
| PCH—5F | 5,0% | Clearing point [°C.]: | +81 |
| PCH—7F | 6,0% | Δn [589 nm, 20° C.]: | 0,0884 |
| CCP—2OCF$_3$ | 11,0% | V$_{(10,0,20)}$ [V]: | 1,23 |
| CCP—3OCF$_3$ | 12,0% | V$_{(90,0,20)}$ [V]: | 1,95 |
| CCP—4OCF$_3$ | 10,0% | | |
| CCP—5OCF$_3$ | 12,0% | | |
| CUP—2OCF$_2$.F.F | 12,0% | | |
| BCH—5F.F.F | 11,0% | | |
| CCP—3F.F.F | 12,0% | | |
| CCP—5F.F.F | 9,0% | | |

Example 30

| | | | |
|---|---|---|---|
| PCH—6F | 5,0% | Clearing point [°C.]: | +85 |
| CCP—2OCF$_2$.F.F | 19,0% | Δn [589 nm, 20° C.]: | 0,0993 |
| CCP—3OCF$_2$.F.F | 19,0% | V$_{(10,0,20)}$ [V]: | 1,23 |
| CCP—5OCF$_2$.F.F | 19,0% | V$_{(90,0,20)}$ [V]: | 1,89 |
| CUP—2F.F | 5,0% | | |
| CUP—3F.F | 5,0% | | |
| CUP—5F.F | 5,0% | | |
| CUP—2OCF$_2$.F.F | 5,0% | | |
| CUP—3OCF$_2$.F.F | 5,0% | | |
| CUP—5OCF$_2$.F.F | 5,0% | | |
| CBC—33F | 4,0% | | |
| CBC—53F | 4,0% | | |

Example 31

| | | | |
|---|---|---|---|
| PCH—6F | 3,5% | Clearing point [°C.]: | +92 |
| PCH—7F | 3,0% | Δn [589 nm, 20° C.]: | +0,0942 |
| CCP—2OCF$_2$.F.F | 16,0% | V$_{(10,0,20)}$ [V]: | 1,25 |
| CCP—3OCF$_2$.F.F | 15,0% | V$_{(90,0,20)}$ [V]: | 1,94 |
| CCP—5OCF$_2$.F.F | 16,0% | | |
| CUP—2F.F | 6,0% | | |
| CUP—3F.F | 6,0% | | |
| CUP—5F.F | 5,0% | | |
| CUP—2OCF$_2$.F.F | 6,0% | | |
| CUP—3OCF$_2$.F.F | 6,0% | | |
| CUP—5OCF$_2$.F.F | 6,0% | | |
| CCPC—33 | 3,5% | | |
| CCPC—34 | 4,0% | | |
| CCPC—35 | 4,0% | | |

Example 32

| | | | |
|---|---|---|---|
| PCH—6F | 4,5% | Clearing point [°C.]: | +86 |
| PCH—7F | 3,0% | Δn [589 nm, 20° C.]: | +0,0952 |
| CCP—2OCF$_2$.F.F | 16,0% | V$_{(10,0,20)}$ [V]: | 1,21 |
| CCP—3OCF$_2$.F.F | 15,0% | V$_{(90,0,20)}$ [V]: | 1,88 |
| CCP—5OCF$_2$.F.F | 16,0% | | |
| CUP—2F.F | 6,0% | | |

-continued

| | | | |
|---|---|---|---|
| CUP—3F.F | 6,0% | | |
| CUP—5F.F | 5,0% | | |
| CUP—2OCF$_2$.F.F | 6,0% | | |
| CUP—3OCF$_2$.F.F | 6,0% | | |
| CUP—5OCF$_2$.F.F | 6,0% | | |
| CCPC—33 | 2,5% | | |
| CCPC—34 | 4,0% | | |
| CCPC—35 | 4,0% | | |

Example 33

| | | | |
|---|---|---|---|
| PCH—5F | 4,5% | Clearing point [°C.]: | +101 |
| CCP—2OCF$_2$.F.F | 16,0% | $\Delta$n [589 nm, 20° C.]: | +0,0984 |
| CCP—3OCF$_2$.F.F | 15,0% | V$_{(10,0,20)}$ [V]: | 1,22 |
| CCP—5OCF$_2$.F.F | 16,0% | V$_{(90,0,20)}$ [V]: | 1,92 |
| CUP—2F.F | 6,0% | | |
| CUP—3F.F | 6,0% | | |
| CUP—5F.F | 5,0% | | |
| CUP—2OCF$_2$.F.F | 6,0% | | |
| CUP—3OCF$_2$.F.F | 6,0% | | |
| CUP—5OCF$_2$.F.F | 6,0% | | |
| CCPC—33 | 4,0% | | |
| CCPC—34 | 4,5% | | |
| CCPC—35 | 5,0% | | |

Example 34

| | | | |
|---|---|---|---|
| CCP—2OCF$_2$.F.F | 16,0% | Clearing point [°C.]: | 96 |
| CCP—3OCF$_2$.F.F | 15,0% | $\Delta$n [589 nm, 20° C.]: | +0,1010 |
| CCP—5OCF$_2$.F.F | 16,0% | V$_{(10,0,20)}$ [V]: | 1,27 |
| CUP—2F.F | 6,0% | V$_{(90,0,20)}$ [V]: | 1,94 |
| CUP—3F.F | 6,0% | | |
| CUP—5F.F | 5,0% | | |
| CUP—2OCF$_2$.F.F | 6,0% | | |
| CUP—3OCF$_2$.F.F | 6,0% | | |
| CUP—5OCF$_2$.F.F | 6,0% | | |
| CBC—33F | 6,0% | | |
| CBC—53F | 6,0% | | |
| CBC—55F | 6,0% | | |

Example 35

| | | | |
|---|---|---|---|
| PCH—6F | 3,5% | Clearing point [°C.]: | 96 |
| PCH—7F | 8,0% | $\Delta$n [589 nm, 20° C.]: | +0,1010 |
| CCP—2OCF$_2$.F.F | 16,0% | V$_{(10,0,20)}$ [V]: | 1,38 |
| CCP—3OCF$_2$.F.F | 15,9% | V$_{(90,0,20)}$ [V]: | 2,10 |
| CCP—5OCF$_2$.F.F | 16,0% | | |
| CUP—2F.F | 6,0% | | |
| CUP—3F.F | 6,0% | | |
| CUP—5F.F | 5,0% | | |
| CUP—2OCF$_2$.F.F | 6,0% | | |
| CUP—3OCF$_2$.F.F | 6,0% | | |
| CUP—5OCF$_2$.F.F | 6,0% | | |
| CBC—33F | 3,5% | | |
| CBC—53F | 4,0% | | |
| CBC—55F | 4,0% | | |

Example 36

| | | | |
|---|---|---|---|
| PCH—5F | 8,5% | Clearing point [°C.]: | 80 |
| PCH—6F | 6,8% | | |
| PCH—7F | 5,1% | | |
| CCP—2OCF$_3$ | 6,8% | | |
| CCP—3OCF$_3$ | 10,2% | | |
| CCP—4OCF$_3$ | 6,0% | | |
| CCP—5OCF$_3$ | 9,3% | | |
| BCH—3F.F | 10,2% | | |
| BCH—5F.F | 8,5% | | |
| ECCP—3OCF$_3$ | 4,2% | | |
| ECCP—5OCF$_3$ | 4,2% | | |
| CBC—33F | 1,7% | | |
| CBC—53F | 1,7% | | |
| CBC—55F | 1,7% | | |
| CUP—3OCF$_2$.F.F | 15,0% | | |

Example 37

| | | | |
|---|---|---|---|
| PCH—7F | 1,0% | Clearing point [°C.]: | +84 |
| CCP—2OCF$_2$.F.F | 16,0% | $\Delta$n [589 nm, 20° C.]: | +0,1050 |
| CCP—3OCF$_2$.F.F | 16,0% | V$_{(10,0,20)}$ [V]: | 1,09 |
| CCP—5OCF$_2$.F.F | 16,0% | V$_{(90,0,20)}$ [V]: | 1,74 |
| CUP—2F.F | 5,0% | | |
| CUP—3F.F | 5,0% | | |
| CUP—5F.F | 5,0% | | |
| CUP—2OCF$_2$.F.F | 5,0% | | |

-continued

| | | | |
|---|---|---|---|
| CUP—3OCF$_2$.F.F | 5,0% | | |
| CUP—5OCF$_2$.F.F | 5,0% | | |
| CUP—2OCCF$_2$.F.F | 5,0% | | |
| CUP—3OCCF$_2$.F.F | 5,0% | | |
| CBC—53F | 3,0% | | |
| CBC—55F | 3,0% | | |

Example 38

| | | | |
|---|---|---|---|
| PCH—5F | 9,0% | Clearing point [°C.]: | +81,6 |
| PCH—6F | 7,2% | $\Delta$n [589 nm, 20° C.]: | 0,0965 |
| PCH—7F | 5,4% | $\Delta\epsilon$ [1 kHz, 20° C.]: | 6,17 |
| CCP—2OCF$_3$ | 7,2% | | |
| CCP—3OCF$_3$ | 10,8% | | |
| CCP—4OCF$_3$ | 8,1% | | |
| CCP—5OCF$_3$ | 8,1% | | |
| BCH—3F.F | 10,8% | | |
| BCH—5F.F | 9,0% | | |
| ECCP—3OCF$_3$ | 4,5% | | |
| ECCP—5OCF$_3$ | 4,5% | | |
| CBC—33F | 1,8% | | |
| CBC—53F | 1,8% | | |
| CBC—55F | 1,8% | | |
| CUP—2OCF$_2$.F.F | 10,0% | | |

Example 39

| | | | |
|---|---|---|---|
| PCH—5F | 9,0% | Clearing point [°C.]: | 84,0 |
| PCH—6F | 7,2% | $\Delta$n [589 nm, 20° C.]: | 0,0980 |
| PCH—7F | 5,4% | $\Delta\epsilon$ [1 kHz, 20° C.]: | 6,18 |
| CCP—2OCF$_3$ | 7,2% | | |
| CCP—3OCF$_3$ | 10,8% | | |
| CCP—4OCF$_3$ | 8,1% | | |
| CCP—5OCF$_3$ | 8,1% | | |
| BCH—3F.F | 10,8% | | |
| BCH—5F.F | 9,0% | | |
| ECCP—3OCF$_3$ | 4,5% | | |
| ECCP—5OCF$_3$ | 4,5% | | |
| CBC—33F | 1,8% | | |
| CBC—53F | 1,8% | | |
| CBC—55F | 1,8% | | |
| CUP—3OCF$_3$.F.F | 10,0% | | |

Example 40

| | | | |
|---|---|---|---|
| PCH—5F | 9,0% | Clearing point [°C.]: | 84,7 |
| PCH—6F | 7,2% | $\Delta$n [589 nm, 20° C.]: | 0,0975 |
| PCH—7F | 5,4% | $\Delta\epsilon$ [1 kHz, 20° C.]: | 6,21 |
| CCP—2OCF$_3$ | 7,2% | | |
| CCP—3OCF$_3$ | 10,8% | | |
| CCP—4OCF$_3$ | 8,1% | | |
| CCP—5OCF$_3$ | 8,1% | | |
| BCH—3F.F | 10,8% | | |
| BCH—5F.F | 9,0% | | |
| ECCP—3OCF$_3$ | 4,5% | | |
| ECCP—5OCF$_3$ | 4,5% | | |
| CBC—33F | 1,8% | | |
| CBC—53F | 1,8% | | |
| CBC—55F | 1,8% | | |
| CUP—5OCF$_2$.F.F | 10,0% | | |

Example 41

| | | | |
|---|---|---|---|
| PCH—6F | 4,5% | S $\rightarrow$ N [°C.]: | <−40 |
| PCH—7F | 4,0% | Clearing point [°C.]: | +84 |
| CCP—2OCF$_2$.F.F | 16,0% | $\Delta$n [589 nm, 20° C.]: | +0,1012 |
| CCP—3OCF$_2$.F.F | 15,0% | V$_{(10,0,20)}$ [V]: | 1,17 |
| CCP—5OCF$_2$.F.F | 16,0% | V$_{(50,0,20)}$ [V]: | 1,47 |
| CUP—2F.F | 6,0% | V$_{(90,0,20)}$ [V]: | 1,87 |
| CUP—3F.F | 6,0% | v 20: | 44 cSt |
| CUP—5F.F | 5,0% | v −40: | 19000 cSt |
| CUP—3OCCF$_2$.F.F | 9,0% | HR (100° C.): | 92% |
| CUP—5OCCF$_2$.F.F | 9,0% | | |
| CBC—33F | 3,5% | | |
| CBC—53F | 3,5% | | |
| CBC—55F | 3,0% | | |

Example 42

| | | | |
|---|---|---|---|
| PCH—5F | 3,0% | S $\rightarrow$ N [°C.]: | |
| CCP—2OCF$_2$.F.F | 16,0% | Clearing point [°C.]: | +109 |
| CCP—3OCF$_2$.F.F | 15,0% | $\Delta$n [589 nm, 20° C.]: | +0,1111 |
| CCP—5OCF$_2$.F.F | 16,0% | $\Delta\epsilon$ [1 kHz, 20° C.]: | |
| CUP—2F.F | 5,0% | V$_{(10,0,20)}$ [V]: | 1,29 |
| CUP—3F.F | 5,0% | V$_{(90,0,20)}$ [V]: | 2,03 |

| | | | |
|---|---|---|---|
| CUP—5F.F | 5,0% | | |
| CUP—3OCCF$_2$.F.F | 10,0% | | |
| CUP—5OCCF$_2$.F.F | 10,0% | | |
| CBC—33F | 5,0% | | |
| CBC—53F | 5,0% | | |
| CBC—55F | 5,0% | | |

Example 43

| | | | |
|---|---|---|---|
| PCH—5F | 6,0% | S → N [°C]: | |
| CCP—2OCF$_2$.F.F | 16,0% | Clearing point [°C]: | +96 |
| CCP—3OCF$_2$.F.F | 15,0% | Δn [589 nm, 20° C.]: | +0,1061 |
| CCP—5OCF$_2$.F.F | 16,0% | Δε [1 kHz, 20° C.]: | |
| CUP—2F.F | 5,0% | V$_{(10,0,20)}$ [V]: | 1,24 |
| CUP—3F.F | 5,0% | V$_{(90,0,20)}$ [V]: | 1,92 |
| CUP—5F.F | 5,0% | | |
| CUP—3OCCF$_2$.F.F | 10,0% | | |
| CUP—5OCCF$_2$.F.F | 10,0% | | |
| CBC—33F | 4,0% | | |
| CBC—53F | 4,0% | | |
| CBC—55F | 4,0% | | |

Example 44

| | | | |
|---|---|---|---|
| PCH—5F | 5,0% | S → N [°C]: | |
| CCP—2OCF$_2$.F.F | 16,0% | Clearing point [°C]: | +100 |
| CCP—3OCF$_2$.F.F | 15,0% | Δn [589 nm, 20° C.]: | +0,1077 |
| CCP—5OCF$_2$.F.F — | 16,0% | Δε [1 kHz, 20° C.]: | |
| CUP—2F.F | 5,0% | V$_{(10,0,20)}$ [V]: | 1,25 |
| CUP—3F.F | 5,0% | V$_{(90,0,20)}$ [V]: | 1,97 |
| CUP—5F.F | 5,0% | | |
| CUP—3OCCF$_2$.F.F | 10,0% | | |
| CUP—5OCCF$_2$.F.F | 10,0% | | |
| CBC—33F | 5,0% | | |
| CBC—53F | 4,5% | | |
| CBC—55F | 3,5% | | |

Example 45

| | | | |
|---|---|---|---|
| PCH—6F | 3,5% | S → N [°C]: | |
| PCH—7F | 3,0% | Clearing point [°C]: | +88 |
| CCP—2OCF$_2$.F.F | 16,0% | Δn [589 nm, 20° C.]: | +0,1036 |
| CCP—3OCF$_2$.F.F | 15,0% | Δε [1 kHz, 20° C.]: | |
| CCP—5OCF$_2$.F.F | 16,0% | V$_{(10,0,20)}$ [V]: | 1,14 |
| CUP—2F.F | 6,0% | V$_{(90,0,20)}$ [V]: | 1,79 |
| CUP—3F.F | 6,0% | | |
| CUP—5F.F | 5,0% | | |
| CUP—3OCCF$_2$.F.F | 10,0% | | |
| CUP—5OCCF$_2$.F.F | 10,0% | | |
| CBC—33F | 3,5% | | |
| CBC—53F | 3,0% | | |
| CBC—55F | 3,0% | | |

Example 46

| | | | |
|---|---|---|---|
| PCH—6F | 5,5% | S → N [°C]: | |
| PCH—7F | 5,0% | Clearing point [°C]: | +81 |
| CCP—2OCF$_2$.F.F | 16,0% | Δn [589 nm, 20° C.]: | +0,0994 |
| CCP—3OCF$_2$.F.F | 15,0% | Δε [1 kHz, 20° C.]: | |
| CCP—5OCF$_2$.F.F | 16,0% | V$_{(10,0,20)}$ [V]: | 1,21 |
| CUP—2F.F | 5,0% | V$_{(90,0,20)}$ [V]: | 1,88 |
| CUP—3F.F | 5,0% | | |
| CUP—5F.F | 5,0% | | |
| CUP—3OCCF$_2$.F.F | 9,0% | | |
| CUP—5OCCF$_2$.F.F | 9,0% | | |
| CBC—33F | 3,5% | | |
| CBC—53F | 3,0% | | |
| CBC—55F | 3,0% | | |

Example 47

| | | | |
|---|---|---|---|
| PCH—6F | 4,5% | S → N [°C]: | <−40 |
| PCH—7F | 4,0% | Clearing point [°C]: | +84 |
| CCP—2OCF$_2$.F.F | 16,0% | Δn [589 nm, 20° C.]: | +0.1012 |
| CCP—3OCF$_2$.F.F | 15,0% | Δε [1 kHz, 20° C.]: | |
| CCP—5OCF$_2$.F.F | 16,0% | V$_{(10,0,20)}$ [V]: | 1,18 |
| CUP—2F.F | 6,0% | V$_{(90,0,20)}$ [V]: | 1,87 |
| CUP—3F.F | 6,0% | | |
| CUP—5F.F | 5,0% | | |
| CUP—3OCCF$_2$.F.F | 9,0% | | |
| CUP—5OCCF$_2$.F.F | 9,0% | | |
| CBC—33F | 3,5% | | |
| CBC—53F | 3,0% | | |
| CBC—55F | 3,0% | | |

Example 48

| | | | |
|---|---|---|---|
| PCH—6F | 4,5% | S → N (°C): | <−40 |
| PCH—7F | 4,0% | Clearing point [°C]: | +93 |
| CCP—2OCF$_2$.F.F | 8,0% | Δn (589 nm, 20° C.): | +0,1036 |
| CCP—3OCF$_2$.F.F | 8,0% | Δε (1 kHz, 20° C.): | |
| CCP—5OCF$_2$.F.F | 8,0% | V$_{(10,0,20)}$ [V]: | 1,21 |
| CCP—2OCCF$_2$.F.F | 8,0% | V$_{(90,0,20)}$ [V]: | 1,92 |
| CCP—3OCCF$_2$.F.F | 7,0% | | |
| CCP—5OCCF$_2$.F.F | 8,0% | | |
| CUP—2F.F | 6,0% | | |
| CUP—3F.F | 6,0% | | |
| CUP—5F.F | 5,0% | | |
| CUP—3OCCF$_2$.F.F | 9,0% | | |
| CUP—5OCCF$_2$.F.F | 9,0% | | |
| CBC—33F | 3,5% | | |
| CBC—53F | 3,0% | | |
| CBC—55F | 3,0% | | |

Example 49

| | | | |
|---|---|---|---|
| PCH—6F | 4,5% | S → N [°C]: | <−40 |
| PCH—7F | 4,0% | Clearing point [°C]: | +96 |
| CCP—2OCCF$_2$.F.F | 16,0% | Δn [589 nm, 20° C.]: | +0,108 |
| CCP—3OCCF$_2$.F.F | 15,0% | Δε [1 kHz, 20° C.]: | |
| CCP—5OCCF$_2$.F.F | 16,0% | V$_{(10,0,20)}$ [V]: | 1,23 |
| CUP—2F.F | 6,0% | V$_{(90,0,20)}$ [V]: | 1,95 |
| CUP—3F.F | 6,0% | | |
| CUP—5F.F | 5,0% | | |
| CUP—3OCCF$_2$.F.F | 9,0% | | |
| CUP—5OCCF$_2$.F.F | 9,0% | | |
| CBC—33F | 3,5% | | |
| CBC—53F | 3,0% | | |
| CBC—55F | 3,0% | | |

Example 50

| | | | |
|---|---|---|---|
| PCH—EF | 4,5% | S → N [°C]: | <−40 |
| PCH—7F | 4,0% | Clearing point [°C]: | +87 |
| CCP—2OCF$_2$.F.F | 16,0% | Δn [589 nm, 20° C.]: | +0,103 |
| CCP—3OCF$_2$.F.F | 15,0% | Δε [1 kHz, 20° C.]: | |
| CCP—5OCF$_2$.F.F | 16,0% | V$_{(10,0,20)}$ [V]: | 1,15 |
| CUP—2OCH=CF$_2$.F.F | 6,0% | V$_{(90,0,20)}$ [V]: | 1,86 |
| CUP—3OCH=CF$_2$.F.F | 6,0% | | |
| CUP—5OCH=CF$_2$.F.F | 5,0% | | |
| CUP—3OCCF$_2$.F.F | 9,0% | | |
| CUP—5OCCF$_2$.F.F | 9,0% | | |
| CBC—33F | 3,5% | | |
| CBC—53F | 3,0% | | |
| CBC—55F | 3,0% | | |

Example 51

| | | | |
|---|---|---|---|
| PCH—6F | 4,5% | S → N [°C]: | <−40 |
| PCH—7F | 4,0% | Clearing point [°C]: | 93 |
| CCP—2OCF=CF$_2$.F.F | 16,0% | Δn [589 nm, 20° C.]: | +0,105 |
| CCP—3OCF=CF$_2$.F.F | 15,0% | Δε (1 kHz, 20° C.): | |
| CCP—5OCF=CF$_2$.F.F | 16,0% | V$_{(10,0,20)}$ [V]: | 1,13 |
| CUP—2F.F | 6,0% | V$_{(90,0,20)}$ [V]: | 1,80 |
| CUP—3F.F | 6,0% | | |
| CUP—5F.F | 5,0% | | |
| CUP—3OCCF$_2$.F.F | 9,0% | | |
| CUP—5OCCF$_2$.F.F | 9,0% | | |
| CBC—33F | 3,5% | | |
| CBC—53F | 3,5% | | |
| CBC—55F | 3,0% | | |

Example 52

| | | | |
|---|---|---|---|
| PCH—5F | 3,0% | S → N [°C]: | |
| CCP—2OCF$_2$.F.F | 16,0% | Clearing point [°C]: | +119 |
| CCP—3OCF$_2$.F.F | 15,0% | Δn [589 nm, 20° C.): | +0,1158 |
| CCP—5OCF$_2$.F.F | 16,0% | Δε [1 kHz, 20° C.]: | |
| CUP—2F.F | 5,0% | V$_{(10,0,20)}$ [V]: | 1,51 |
| CUP—3F.F | 5,0% | V$_{(90,0,20)}$ [V]: | 2,34 |
| CUP—5F.F | 5,0% | | |
| BCH—3OCCF$_2$.F.F | 10,0% | | |
| BCH—5OCCF$_2$.F.F | 10,0% | | |
| CBC—33F | 5,0% | | |
| CBC—53F | 5,0% | | |
| CBC—55F | 5,0% | | |

Example 53

| | | | |
|---|---|---|---|
| PCH—5F | 3,0% | S → N [°C]: | |

-continued

| | | | |
|---|---|---|---|
| CCP—2OCF$_2$.F.F | 16,0% | Clearing point [°C.]: | +96 |
| CCP—3OCF$_2$.F.F | 15,0% | Δn [589 nm, 20° C.]: | +0,1061 |
| CCP—5OCF$_2$.F.F | 16,0% | Δε [1 kHz, 20° C.]: | |
| CUP—2F.F | 5,0% | V$_{(10,0,20)}$ [V]: | 1,24 |
| CUP—3F.F | 5,0% | V$_{(90,0,20)}$ [V]: | 1,92 |
| CUP—5F.F | 5,0% | | |
| CUP—3OCCF$_2$.F.F | 10,0% | | |
| CUP—5OCCF$_2$.F.F | 10,0% | | |
| CBC—33F | 4,0% | | |
| CBC—53F | 4,0% | | |
| CBC—55F | 4,0% | | |

Example 54

| | | | |
|---|---|---|---|
| PCH—5F | 5,0% | S → N [°C.]: | |
| CCP—2OCF$_2$.F.F | 16,0% | Clearing point [°C.]: | +100 |
| CCP—3OCF$_2$.F.F | 15,0% | Δn [589 nm, 20° C.]: | +0,1077 |
| CCP—5OCF$_2$.F.F | 16,0% | Δε [1 kHz, 20° C.]: | |
| CUP—2F.F | 5,0% | V$_{(10,0,20)}$ [V]: | 1,25 |
| CUP—3F.F | 5,0% | V$_{(90,0,20)}$ [V]: | 1,97 |
| CUP—5F.F | 5,0% | | |
| CUP—3OCCF$_2$.F.F | 10,0% | | |
| CUP—5OCCF$_2$.F.F | 10,0% | | |
| CBC—33F | 5,0% | | |
| CBC—53F | 4,5% | | |
| CBC—55F | 3,5% | | |

Example 55

| | | | |
|---|---|---|---|
| PCH—5F | 5,0% | S → N [°C.]: | |
| PCH—7F | 6,0% | Clearing point [°C.]: | +85 |
| CCP—2OCF$_3$ | 11,0% | Δn [589 nm, 20° C.]: | +0,0922 |
| CCP—3OCF$_3$ | 12,0% | Δε [1 kHz, 20° C.]: | |
| CCP—4OCF$_3$ | 10,0% | V$_{(10,0,20)}$ [V]: | 1,41 |
| CCP—5OCF$_3$ | 12,0% | V$_{(90,0,20)}$ [V]: | 2,20 |
| CUP—3OCH=CF$_2$.F.F | 12,0% | | |
| CUP—5OCH=CF$_2$.F.F | 11,0% | | |
| CCP—3F.F.F | 12,0% | | |
| CCP—5F.F.F | 9,0% | | |

Example 56

| | | | |
|---|---|---|---|
| PCH—5F | 3,0% | S → N [°C.]: | |
| CCP—2OCF$_2$.F.F | 16,0% | Clearing point [°C.]: | +106 |
| CCP—3OCF$_2$.F.F | 15,0% | Δn [589 nm, 20° C.]: | +0,1117 |
| CCP—5OCF$_2$.F.F | 16,0% | Δε [1 kHz, 20° C.]: | |
| CUP—2F.F | 5,0% | V$_{(10,0,20)}$ [V]: | 1,24 |
| CUP—3F.F | 5,0% | V$_{(90,0,20)}$ [V]: | 1,94 |
| CUP—5F.F | 5,0% | | |
| CUP—3OCH=CF$_2$.F.F | 10,0% | | |
| CUP—5OCH=CF$_2$.F.F | 10,0% | | |
| CBC—33F | 5,0% | | |
| CBC—53F | 5,0% | | |
| CBC—55F | 5,0% | | |

Example 57

| | | | |
|---|---|---|---|
| PCH—5F | 4,5% | Clearing point [°C.]: | +99 |
| CCP—2OCF$_2$.F.F | 16,0% | Δn [589 nm, 20° C.]: | +0,1091 |
| CCP—3OCF$_2$.F.F | 15,0% | V$_{(10,0,20)}$ [V]: | 1,12 |
| CCP—5OCF$_2$.F.F | 16,0% | V$_{(90,0,20)}$ [V]: | 1,81 |
| CUP—2F.F | 5,0% | | |
| CUP—3F.F | 5,0% | | |
| CUP—5F.F | 5,0% | | |
| CUP—3OCH=CF$_2$.F.F | 10,0% | | |
| CUP—5OCH=CF$_2$.F.F | 10,0% | | |
| CBC—33F | 5,0% | | |
| CBC—53F | 4,5% | | |
| CBC—55F | 4,0% | | |

Example 58

| | | | |
|---|---|---|---|
| PCH—5F | 4,0% | Clearing point [°C.]: | +101 |
| CCP—2OCF$_2$.F.F | 16,0% | Δn (589 nm, 20° C.]: | +0,1098 |
| CCP—3OCF$_2$.F.F | 15,0% | V$_{(10,0,20)}$ [V]: | 1,04 |
| CCP—5OCF$_2$.F.F | 16,0% | V$_{(90,0,20)}$ [V]: | 1,68 |
| CUP—2F.F | 5,0% | | |
| CUP—3F.F | 5,0% | | |
| CUP—5F.F | 5,0% | | |
| CUP—3OCH=CF$_2$.F.F | 10,0% | | |
| CUP—5OCH=CF$_2$.F.F | 10,0% | | |
| CBC—33F | 5,0% | | |
| CBC—53F | 5,0% | | |
| CBC—55F | 4,0% | | |

Example 59

| | | | |
|---|---|---|---|
| PCH—6F | 4,0% | Clearing point [°C.]: | +85 |
| PCH—7F | 3,0% | Δn [589 nm, 20° C.]: | +0,1030 |
| CCP—2OCF$_2$.F.F | 16,0% | V$_{(10,0,20)}$ [V]: | 1,15 |
| CCP—3OCF$_2$.F.F | 15,0% | V$_{(90,0,20)}$ [V]: | 1,79 |
| CCP—5OCF$_2$.F.F | 17,0% | | |
| CUP—2F.F | 6,0% | | |
| CUP—3F.F | 6,0% | | |
| CUP—5F.F | 5,0% | | |
| CUP—3OCH=CF$_2$.F.F | 9,0% | | |
| CUP—5OCH=CF$_2$.F.F | 9,0% | | |
| CBC—33F | 4,0% | | |
| CBC—53F | 3,0% | | |
| CBC—55F | 3,0% | | |

Example 60

| | | | |
|---|---|---|---|
| PCH—6F | 3,0% | Clearing point [°C.]: | +87 |
| CCP—2OCF$_2$.F.F | 16,0% | Δn [589 nm, 20° C.]: | +0,1071 |
| CCP—3OCF$_2$.F.F | 15,0% | V$_{(10,0,20)}$ [V]: | 1,11 |
| CCP—5OCF$_2$.F.F | 16,0% | V$_{(90,0,20)}$ [V]: | 1,74 |
| CUP—2F.F | 7,0% | | |
| CUP—3F.F | 7,0% | | |
| CUP—5F.F | 7,0% | | |
| CUP—3OCH=CF$_2$.F.F | 10,0 | | |
| CUP—5OCH=CF$_2$.F.F | 10,0% | | |
| CBC—33F | 3,0% | | |
| CBC—53F | 3,0% | | |
| CBC—55F | 3,0% | | |

Example 61

| | | | |
|---|---|---|---|
| PCH—5F | 3,0% | Clearing point [°C.]: | +84 |
| CCP—2OCF$_2$.F.F | 17,0% | Δn [589 nm, 20° C.]: | +0,1061 |
| CCP—3OCF$_2$.F.F | 15,0% | V$_{(10,0,20)}$ [V]: | 1,10 |
| CCP—5OCF$_2$.F.F | 16,0% | V$_{(90,0,20)}$ [V]: | 1,72 |
| CUP—2F.F | 7,0% | | |
| CUP—3F.F | 7,0% | | |
| CUP—5F.F | 7,0% | | |
| CUP—3OCH=CF$_2$.F.F | 10,0% | | |
| CUP—5OCH=CF$_2$.F.F | 10,0% | | |
| CBC—33F | 3,0% | | |
| CBC—53F | 3,0% | | |
| CBC—55F | 2,0% | | |

Example 62

| | | | |
|---|---|---|---|
| PCH—5F | 4,0% | Clearing point [°C.]: | +101 |
| CCP—2OCF$_2$.F.F | 16,0% | Δn [589 nm, 20° C.]: | +0,1105 |
| CCP—3OCF$_2$.F.F | 15,0% | V$_{(10,0,20)}$ [V]: | 1,24 |
| CCP—5OCF$_2$.F.F | 16,0% | V$_{(90,0,20)}$ [V]: | 1,93 |
| CUP—2F.F | 5,0% | | |
| CUP—3F.F | 5,0% | | |
| CUP—5F.F | 5,0% | | |
| CUP—3OCH=CF$_2$.F.F | 10,0% | | |
| CUP—5OCH=CF$_2$.F.F | 10,0% | | |
| CBC—33F | 5,0% | | |
| CBC—53F | 5,0% | | |
| CBC—55F | 4,0% | | |

Example 63

| | | | |
|---|---|---|---|
| PCH—5F | 9,0% | Clearing point [°C.]: | 84,6 |
| PCH—6F | 7,2% | Δn [589 nm, 20° C.]: | 0,0996 |
| PCH—7F | 5,4% | Δε [1 kHz, 20° C.]: | 6,37 |
| CCP—2OCF$_3$ | 7,2% | | |
| CCP—3OCF$_3$ | 10,8% | | |
| CCP—4OCF$_3$ | 8,1% | | |
| CCP—5OCF$_3$ | 8,1% | | |
| BCH—3F.F | 10,8% | | |
| BCH—5F.F | 9,0% | | |
| ECCP—3OCF$_3$ | 4,5% | | |
| ECCP—5OCF$_3$ | 4,5% | | |
| CBC—33F | 1,8% | | |
| CBC—53F | 1,8% | | |
| CBC—55F | 1,8% | | |
| CUP—2OCH=CF$_2$.F.F | 10,0% | | |

Example 64

| | | | |
|---|---|---|---|
| PCH—5F | 9,0% | Clearing point [°C.]: | 87,3 |
| PCH—6F | 7,2% | Δn [589 nm, 20°C.]: | 0,0995 |
| PCH—7F | 5,4% | Δε [1 kHz, 20° C.]: | 6,22 |
| CCP—2OCF$_3$ | 7,2% | | |
| CCP—3OCF$_3$ | 10,8% | | |

| | | | |
|---|---|---|---|
| CCP—4OCF₃ | 8,1% | | |
| CCP—5OCF₃ | 8,1% | | |
| BCH—3F.F | 10,8% | | |
| BCH—5F.F | 9,0% | | |
| ECCP—3OCF₃ | 4,5% | | |
| ECCP—5OCF₃ | 4,5% | | |
| CBC—33F | 1,8% | | |
| CBC—53F | 1,8% | | |
| CBC—55F | 1,8% | | |
| CUP—5OCH=CF₂.F.F | 10,0% | | |

Example 65

| | | | |
|---|---|---|---|
| PCH—5F | 9,0% | Clearing point [°C]: | 86,6 |
| PCH—6F | 7,2% | Δn [589 nm, 20° C.]: | 0,0994 |
| PCH—7F | 5,4% | Δε [1 kHz, 20° C.]: | 6,48 |
| CCP—2OCF₃ | 7,2% | | |
| CCP—3OCF₃ | 10,8% | | |
| CCP—4OCF₃ | 8,1% | | |
| CCP—5OCF₃ | 8,1% | | |
| BCH—3F.F | 10,8% | | |
| BCH—5F.F | 9,0% | | |
| ECCP—3OCF₃ | 4,5% | | |
| ECCP—5OCF₃ | 4,5% | | |
| CBC—33F | 1,8% | | |
| CBC—53F | 1,8% | | |
| CBC—55F | 1,8% | | |
| CUP—3OCH=CF₂.F.F | 10,0% | | |

Example 66

| | | | |
|---|---|---|---|
| PCH—5F | 9,0% | Clearing point [°C]: | 87,6 |
| PCH—6F | 7,2% | Δn [589 nm, 20° C.]: | +0,0985 |
| PCH—7F | 5,4% | Δε [1 kHz, 20° C.]: | 6,61 |
| CCP—2OCF₃ | 7,2% | | |
| CCP—3OCF₃ | 10,8% | | |
| CCP—4OCF₃ | 8,1% | | |
| CCP—5OCF₃ | 8,1% | | |
| BCH—3F.F | 10,8% | | |
| BCH—5F.F | 9,0% | | |
| ECCP—3OCF₃ | 4,5% | | |
| ECCP—5OCF₃ | 4,5% | | |
| CBC—33F | 1,8% | | |
| CBC—53F | 1,8% | | |
| CBC—55F | 1,8% | | |
| CUP—3OC₂F₅.F.F | 10,0% | | |

Example 67

| | | | |
|---|---|---|---|
| PCH—5F | 9,0% | Clearing point [°C]: | 89 |
| PCH—6F | 7,2% | Δn [589 nm, 20° C.]: | +0,0985 |
| PCH—7F | 5,4% | Δε [1 kHz, 20° C.]: | 6,55 |
| CCP—2OCF₃ | 7,2% | | |
| CCP—3OCF₃ | 10,8% | | |
| CCP—4OCF₃ | 8,1% | | |
| CCP—5OCF₃ | 8,1% | | |
| BCH—3F.F | 10,8% | | |
| BCH—5F.F | 9,0% | | |
| ECCP—3OCF₃ | 4,5% | | |
| ECCP—5OCF₃ | 4,5% | | |
| CBC—33F | 1,8% | | |
| CBC—53F | 1,8% | | |
| CBC—55F | 1,8% | | |
| CUP—5OC₂F₅.F.F | 10,0% | | |

Example 68

| | | | |
|---|---|---|---|
| PCH—5F | 9,0% | Clearing point [°C]: | 90,3 |
| PCH—6F | 7,2% | Δn [589 nm, 20° C.]: | +0,0993 |
| PCH—7F | 5,4% | Δε [1 kHz, 20° C.]: | 6,22 |
| CCP—2OCF₃ | 7,2% | | |
| CCP—3OCF₃ | 10,8% | | |
| CCP—4OCF₃ | 8,1% | | |
| CCP—5OCF₃ | 8,1% | | |
| BCH—3F.F | 10,8% | | |
| BCH—5F.F | 9,0% | | |
| ECCP—3OCF₃ | 4,5% | | |
| ECCP—5OCF₃ | 4,5% | | |
| CBC—33F | 1,8% | | |
| CBC—53F | 1,8% | | |
| CBC—55F | 1,8% | | |
| CUP—5OC₂F₅.F | 10,0% | | |

Example 69

| | | | |
|---|---|---|---|
| PCH—5F | 9,0% | Clearing point [°C]: | 89,3 |
| PCH—6F | 7,2% | Δn [589 nm, 20° C.]: | +0,0993 |
| PCH—7F | 5,4% | Δε [1 kHz, 20° C.]: | 6,27 |
| CCP—2OCF₃ | 7,2% | | |
| CCP—3OCF₃ | 10,8% | | |
| CCP—4OCF₃ | 8,1% | | |
| CCP—5OCF₃ | 8,1% | | |
| BCH—3F.F | 10,8% | | |
| BCH—5F.F | 9,0% | | |
| ECCP—3OCF₃ | 4,5% | | |
| ECCP—5OCF₃ | 4,5% | | |
| CBC—33F | 1,8% | | |
| CBC—53F | 1,8% | | |
| CBC—55F | 1,8% | | |
| CUP—3OC₂F₅.F | 10,0% | | |

We claim:

1. A liquid-crystalline medium based on a mixture of polar compounds having positive dielectric anisotropy, which comprises one or more compounds of the formula I

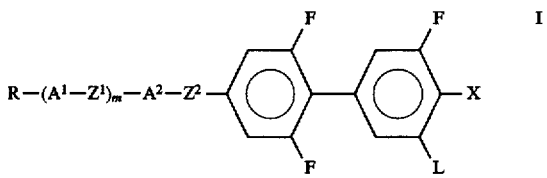

in which

R is H, an alkyl or alkenyl radical having 1 to 15 carbon atoms which is unsubstituted or, optionally, has one or more $CH_2$ groups replaced, in each case independently of one another, by —O—, —S—, —◊—, —CO—, —CO—O—, —O—CO— or —O—CO—O—, such that O atoms are not linked directly to one another, $A^1$ and $A^2$ are each, independently of one another, a
(a) trans-1,4-cyclohexylene racial, which is optionally substituted by one or two fluorine atoms and in which one or more non-adjacent $CH_2$ groups are optionally replaced independently by —O— or —S—,
(b) 1,4-phenylene radical in which one or two CH groups are optionally replaced by N, or
(c) radical selected from the group consisting of 1,4-cyclohexenylene, 1,4-bicyclo(2,2,2)-octylene, piperidine-1,4-diyl, naphthalene-2,6-diyl and 1,2,3,4-tetrahydronaphthalene-2,6-diyl, $Z^1$ and $Z^2$ are each, independently of one another, —CO—O—, —O—CO—, —$CH_2$O—, —O$CH_2$—, —CH=CH—, —C≡C— and one of the radicals $Z^1$ and $Z^2$ is optionally —$(CH_2)_4$— or —CH=CH—$CH_2CH_2$—, X is halogenated alkyl, alkoxy, alkenyl or alkenyloxy, in each case having 1 to 6 carbon atoms, L is F and also H when X is $OC_2F_5$, and m is 0, 1 or 2.

2. The medium according to claim 1, further comprising one or more compounds selected from the group consisting of the compounds of formulae II, III, IV and V:

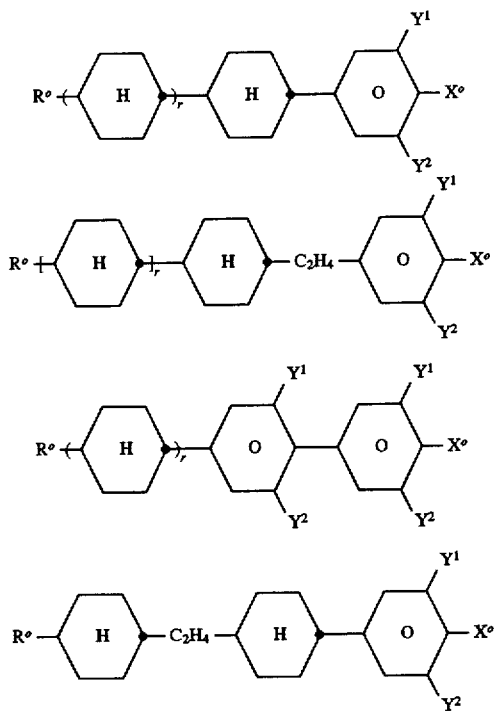

in which the individual radicals are as defined below:

$R^0$: alkyl, oxaalkyl, fluoroalkyl or alkenyl, in each case having 1 to 7 carbon atoms, $X^0$: F, Cl, $CF_3$, $OCF_3$, $OCHF_2$, $OCH=CF_2$, $OCF=CF_2$, $OCFH-CF_2H$ or $OCF_2-CF_2H$, $Y^1$ and $Y^2$: each, independently of one another, H or F r: 0 or 1.

3. The medium according to claim 1, further comprising one or more compounds selected from the group consisting of compounds of formulae VI to XII:

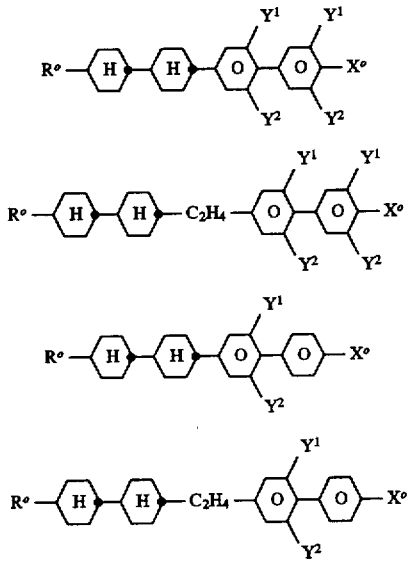

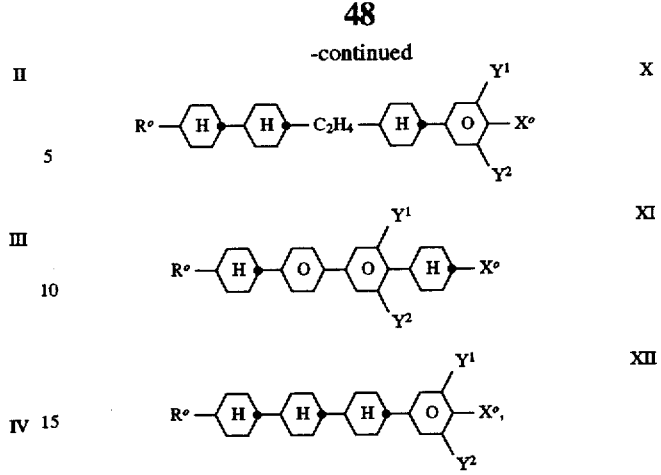

in which the radicals $R^0$, $X^0$, $Y^1$ and $Y^2$ are as defined below:

$R^0$: alkyl, oxaalkyl, fluoroalkyl or alkenyl, in each case having 1 to 7 carbon atoms, $X^0$: F, Cl, $CF_3$, $OCF_3$, $OCHF_2$, $OCH=CF_2$, $OCF=CF_2$, $OCFH-CF_2H$ or $OCF_2-CF_2H$, $Y^1$ and $Y^2$: each, independently of one another, H or F.

4. The medium according to claim 2, wherein the proportion of compounds of the formulae I to V together is at least 50% by weight in the total mixture.

5. The medium according to claim 1, wherein the proportion of compounds of the formula I is from 3 to 80% by weight in the total mixture.

6. The medium according to claim 2, wherein the proportion of compounds of the formulae II to V is from 20 to 80% by weight in the total mixture.

7. The medium according to claim 2, further comprising one or more compounds selected from the group consisting of compounds of formulae VI to XII:

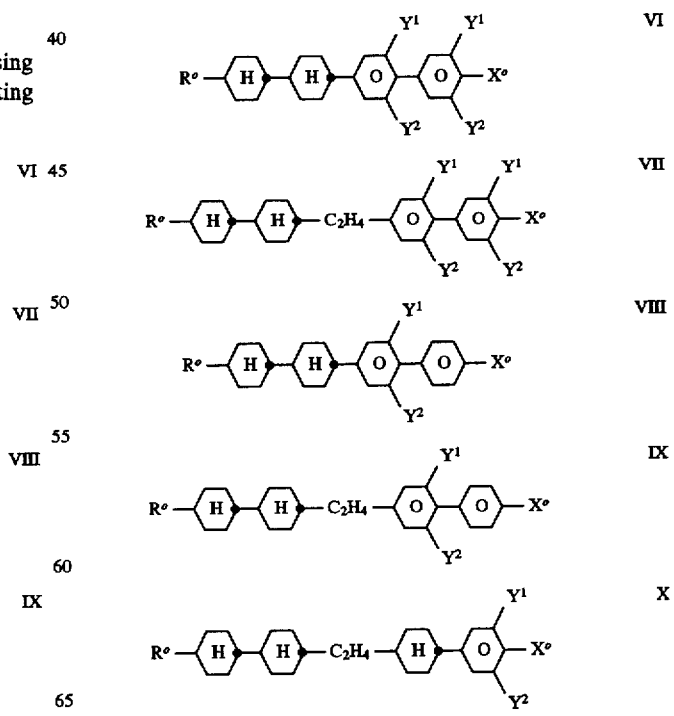

-continued

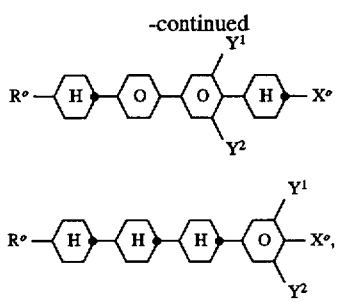

in which the radicals $R^0$, $X^0$, $Y^1$ and $Y^2$ are as defined below:

$R^0$: alkyl, oxaalkyl, fluoroalkyl or alkenyl, in each case having 1 to 7 carbon atoms, $X^0$: F, Cl, $CF_3$, $OCF_3$, $OCHF_2$, $OCH=CF_2$, $OCF=CF_2$, $OCFH—CF_2H$ or $OCF_2—CF_2H$, $Y^1$ and $Y^2$: each, independently of one another, H or F.

8. Electrooptical liquid-crystal display containing a liquid-crystalline medium according to claim 1.

9. The medium according to claim 7, which consists essentially of compounds of the formulae I to XII.

10. The liquid-crystalline medium of claim 1, having a nematic phase range of -20° C. to 80° C., a clearing point above 80° C., a dielectric anisotropy of ≧6 and a TN threshold of below 2.0 V.

11. The liquid-crystalline medium of claim 2, which comprises one or more compounds of the formulae II or III wherein $X^0$ is $OCF_3$, $OCHF_2$, F, $OCH=CF_2$, $OCF=CF_2$, or $OCF_2—CF_2H$.

12. The liquid-crystalline medium of claim 1, which contains only up to about 10% by weight of compounds having nitrile groups.

13. The liquid-crystalline medium of claim 1, which contains no compounds having nitrile groups.

14. The liquid-crystalline medium of claim 1, wherein in formula I, L is F.

15. A liquid crystal mixture based on a mixture of polar compounds having positive dielectric anisotropy which comprises one or more compounds of the formula

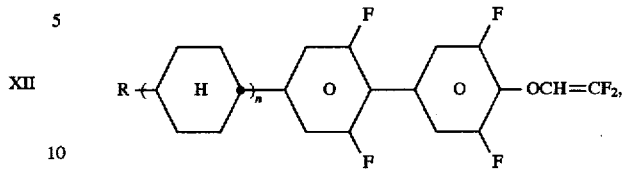

in which

R is H, an alkyl or alkenyl having 1 to 15 carbon atoms which is unsubstituted or, optionally, has one or more CH2 groups replaced, in each case independently of one another, by —O—, —S—, ◊, —CO, —CO—O, —O—CO— or —O—CO—O, such that O atoms are not linked directly to one another.

16. A liquid crystal mixture based on a mixture of polar compounds having no positive dielectric anisotropy which comprises one or more compounds of the formula

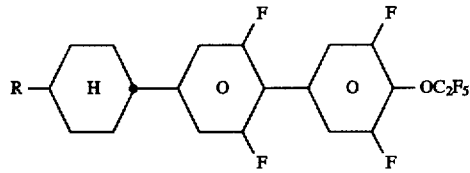

in which

R is H, an alkyl or alkenyl having 1 to 15 carbon atoms which is unsubstituted or, optionally, has one or more CH2 groups replaced, in each case independently of one another, by —O—, —S—, ◊, —CO, —CO—O, —O—CO— or —O—CO—O, such that O atoms are not linked directly to one another.

* * * * *